(12) United States Patent
Abuzaina et al.

(10) Patent No.: US 7,858,835 B2
(45) Date of Patent: Dec. 28, 2010

(54) FOAM CONTROL FOR SYNTHETIC ADHESIVE/SEALANT

(75) Inventors: Ferass Abuzaina, Shelton, CT (US); Fatima Munoz, Danbury, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 766 days.

(21) Appl. No.: 11/823,341

(22) Filed: Jun. 27, 2007

(65) Prior Publication Data

US 2009/0005716 A1   Jan. 1, 2009

(51) Int. Cl.
A61F 13/00 (2006.01)

(52) U.S. Cl. .............................. 602/42; 602/43; 602/48

(58) Field of Classification Search ............. 602/42–54; 424/423, 78, 27, 78.27
See application file for complete search history.

(56) References Cited

U.S. PATENT DOCUMENTS

| | | | |
|---|---|---|---|
| 3,631,138 A | 12/1971 | Peters | |
| 3,773,595 A | 11/1973 | Burba et al. | |
| 4,061,662 A | 12/1977 | Marans et al. | |
| 4,169,175 A | 9/1979 | Marans et al. | |
| 4,323,491 A | 4/1982 | Veselovsky et al. | |
| 4,359,049 A | 11/1982 | Redl et al. | |
| 4,361,055 A | 11/1982 | Kinson | |
| 4,425,472 A | 1/1984 | Howard et al. | |
| 4,650,817 A | 3/1987 | Allen, Jr. et al. | |
| 4,743,632 A | 5/1988 | Marinovic | |
| 4,804,691 A | 2/1989 | English et al. | |
| 4,874,368 A | 10/1989 | Miller et al. | |
| 4,978,336 A | 12/1990 | Capozzi et al. | |
| 4,979,942 A | 12/1990 | Wolf et al. | |
| 5,073,298 A | 12/1991 | Gentle et al. | |
| 5,166,300 A | 11/1992 | Rumon et al. | |
| 5,169,561 A | 12/1992 | Gentle et al. | |
| 5,169,720 A | 12/1992 | Braatz et al. | |
| 5,175,228 A | 12/1992 | Wang et al. | |
| 5,368,563 A | 11/1994 | Lonneman et al. | |
| 5,462,536 A | 10/1995 | Braatz et al. | |
| 5,703,158 A | 12/1997 | Duan et al. | |
| 5,717,030 A | 2/1998 | Dunn et al. | |
| 5,990,237 A | 11/1999 | Bentley et al. | |
| 5,998,540 A | 12/1999 | Lipkin et al. | |
| 6,071,530 A | 6/2000 | Polson | |

(Continued)

FOREIGN PATENT DOCUMENTS

EP    0 077 192 A2    4/1983

(Continued)

OTHER PUBLICATIONS

International Search Report from PCT/US06/47013 dated Oct. 3, 2007.

(Continued)

*Primary Examiner*—Michael A. Brown

(57) ABSTRACT

Methods for producing biocompatible compositions are provided. The biocompatible compositions include an isocyanate-functional polyurethane prepolymer in combination with a foam control agent. The foam control agent decreases the formation of bubbles and/or foam in the biocompatible composition, thereby enhancing the physical properties of the biocompatible composition. The presence of the foam control agent does not compromise the strength of the biocompatible composition. The compositions prepared by the methods of the present disclosure may be used as adhesives or sealants for medical/surgical uses.

17 Claims, 9 Drawing Sheets

U.S. PATENT DOCUMENTS

| | | | |
|---|---|---|---|
| 6,103,850 | A | 8/2000 | Reichel et al. |
| 6,162,241 | A | 12/2000 | Coury et al. |
| 6,261,544 | B1 | 7/2001 | Coury et al. |
| 6,262,176 | B1 | 7/2001 | Kim et al. |
| 6,395,823 | B1 | 5/2002 | Brink et al. |
| 6,489,397 | B2 | 12/2002 | Kim et al. |
| 6,495,127 | B1 | 12/2002 | Wallace et al. |
| 6,527,749 | B1 | 3/2003 | Roby et al. |
| 6,582,713 | B2 | 6/2003 | Newell et al. |
| 6,919,076 | B1 * | 7/2005 | Green et al. ............... 424/94.5 |
| 2003/0032734 | A1 | 2/2003 | Roby |
| 2004/0023842 | A1 | 2/2004 | Pathak et al. |
| 2004/0068078 | A1 | 4/2004 | Milbocker |
| 2004/0115229 | A1 | 6/2004 | Roby |
| 2004/0171745 | A1 | 9/2004 | Kim et al. |
| 2004/0198901 | A1 | 10/2004 | Graham et al. |
| 2005/0004661 | A1 | 1/2005 | Lewis et al. |
| 2005/0013793 | A1 * | 1/2005 | Beckman et al. ......... 424/78.27 |
| 2005/0069573 | A1 | 3/2005 | Cohn et al. |
| 2005/0070913 | A1 * | 3/2005 | Milbocker et al. ............ 606/92 |
| 2005/0075471 | A1 | 4/2005 | Fan et al. |
| 2005/0129733 | A1 * | 6/2005 | Milbocker et al. .......... 424/423 |
| 2005/0142162 | A1 | 6/2005 | Hunter et al. |
| 2005/0147647 | A1 | 7/2005 | Glauser et al. |
| 2005/0266086 | A1 | 12/2005 | Sawhney |
| 2005/0288430 | A1 | 12/2005 | Gindin et al. |
| 2005/0288431 | A1 | 12/2005 | Gindin et al. |
| 2006/0173151 | A1 | 8/2006 | Kim et al. |
| 2006/0182922 | A1 | 8/2006 | Ishida et al. |
| 2006/0183849 | A1 | 8/2006 | Liu et al. |
| 2006/0183850 | A1 | 8/2006 | Liu et al. |
| 2006/0183851 | A1 | 8/2006 | Liu et al. |
| 2006/0183852 | A1 | 8/2006 | Liu et al. |
| 2007/0128152 | A1 | 6/2007 | Hadba et al. |
| 2007/0135605 | A1 | 6/2007 | Hadba et al. |
| 2007/0135606 | A1 | 6/2007 | Belcheva et al. |

FOREIGN PATENT DOCUMENTS

| | | |
|---|---|---|
| EP | 0482467 A | 4/1992 |
| EP | 1223183 A | 7/2002 |
| EP | 1 391 205 A1 | 2/2005 |
| EP | 1 719 530 A | 11/2006 |
| GB | 985 144 | 3/1965 |
| GB | 1 143 309 | 2/1969 |
| GB | 1 187 362 | 4/1970 |
| JP | 2002060341 | 2/2002 |
| WO | WO 01/00246 A | 1/2001 |
| WO | WO 01/16210 A | 3/2001 |
| WO | WO 2007/067623 A | 6/2007 |

OTHER PUBLICATIONS

International Search Report from PCT/US06/46558 dated Nov. 9, 2007.
International Search Report from PCT/US06/46552 dated Nov. 15, 2007.
International Search Report from PCT/US06/47023 dated Nov. 21, 2007.
European Search Report for EP 08252131.1-2115 date of completion is Nov. 2, 2009 (3 pages).
European Search Report for Appln. No. EP 08 25 1790.5 completed Jun. 19, 2009.
Ferreira, et al., "Modification of the Biopolymer Castor Oil With Free Isocyanate Groups to Be Applied As Bioadhesive", *International Journal of Biological Macromolecules*, vol. 40, No. 2, pp. 144-152 (2007).
Ferreira, et al., "Development of a Biodegradable Bioadhesive Containing Urethane Groups", *Journal of Materials Science: Materials in Medicine*, vol. 19, No. 1, pp. 111-120 (2007).
International Search Report from European Application No. EP 08 25 3645 mailed Mar. 5, 2009.
European Search Report for Appln. No. EP 08 25 3647 completed Mar. 6, 2009.
International Search Report from Application No. PCT/US08/60971 dated Jul. 18, 2008.
International Search Report from Application EP 07 00 1213 dated Sep. 6, 2007.
International Search Report from Application EP 03 77 9244 dated Sep. 26, 2007.
International Search Report from Application PCT/US2006/46553 dated Oct. 31, 2007.
International Search Report from Application PCT/US2006/46554 dated Oct. 31, 2007.

* cited by examiner

| | time | thickness (mm) | | | diameter (mm) | | | | weight (mg) | | | | volume (mm^3) | | | |
|---|---|---|---|---|---|---|---|---|---|---|---|---|---|---|---|---|
| | | 0 | 4 hrs | 26 hrs | 4 days | 0 | 4 hrs | 26 hrs | 4 days | 0 | 4 hrs | 26 hrs | 4 days | 0 | 4 hrs | 26 hrs | 4 days |
| A Samples w/0.5% surfynol | a | 0.15 | 0.18 | 0.15 | 0.18 | 7.30 | 9.11 | 9.82 | 9.81 | 9.6 | 20.5 | 20.1 | 20.7 | 6.27808 | 11.7327 | 11.3607 | 13.6051 |
| | b | 0.19 | 0.20 | 0.24 | 0.19 | 7.30 | 9.34 | 9.74 | 9.79 | 10.5 | 23.3 | 22.5 | 24.1 | 7.95223 | 13.7029 | 17.8821 | 14.3024 |
| | c | 0.17 | 0.19 | 0.20 | 0.25 | 7.30 | 9.31 | 9.72 | 9.93 | 10.2 | 23.5 | 23.8 | 24.5 | 7.11516 | 12.9343 | 14.8406 | 19.361 |
| | d | 0.17 | 0.21 | 0.19 | 0.18 | 7.30 | 9.57 | 9.69 | 10.00 | 10 | 22.3 | 22.9 | 22.2 | 7.11516 | 15.1054 | 14.0117 | 14.1372 |
| | e | 0.18 | 0.24 | 0.23 | 0.22 | 7.30 | 9.55 | 9.42 | 9.78 | 10.2 | 24.7 | 24.8 | 26.1 | 7.5337 | 17.1913 | 16.0295 | 16.5269 |
| A Samples w/0.5% DSP | a | 0.20 | 0.18 | 0.27 | 0.26 | 7.30 | 9.33 | 9.77 | 10.03 | 9.4 | 21.4 | 21.1 | 21.8 | 8.37077 | 12.3062 | 20.2415 | 20.5431 |
| | b | 0.17 | 0.16 | 0.18 | 0.20 | 7.30 | 9.44 | 10.04 | 10.02 | 8.9 | 20.6 | 20.3 | 18.4 | 7.11516 | 11.1983 | 14.2505 | 15.7709 |
| | c | 0.15 | 0.16 | 0.20 | 0.17 | 7.30 | 9.63 | 9.83 | 10.15 | 9.5 | 22.2 | 22.2 | 22.7 | 6.27808 | 11.6537 | 15.1784 | 13.7553 |
| | d | 0.17 | 0.15 | 0.22 | 0.19 | 7.30 | 9.70 | 10.22 | 9.64 | 9.1 | 19.8 | 19.38 | / | 7.11516 | 11.0847 | 18.0474 | 13.8675 |
| | e | 0.21 | 0.19 | 0.25 | 0.21 | 7.30 | 9.52 | 10.15 | 9.97 | 10.4 | 23.9 | 24.8 | 24.3 | 8.78931 | 13.5244 | 20.2284 | 16.3945 |
| A Samples w/9% NaHCO3 | a | 0.17 | 0.18 | 0.22 | 0.31 | 7.30 | 9.28 | 9.52 | 10.12 | 8.2 | 17.2 | 18.2 | 19.8 | 7.11516 | 12.1747 | 16.6963 | 24.9352 |
| | b | 0.15 | 0.19 | 0.21 | 0.23 | 7.30 | 9.67 | 9.42 | 10.07 | 8.5 | 18.2 | 18.6 | 20.4 | 6.27808 | 13.9539 | 14.6356 | 18.3179 |
| | c | 0.19 | 0.16 | 0.26 | 0.23 | 7.30 | 9.80 | 9.82 | 10.10 | 8.5 | 18.2 | 18.3 | 20.2 | 7.95223 | 12.0687 | 19.6918 | 18.4272 |
| | d | 0.16 | 0.19 | 0.21 | 0.22 | 7.30 | 9.66 | 9.54 | 10.05 | 8.8 | 18.7 | 18.9 | 21.7 | 6.69662 | 13.9251 | 15.0109 | 17.452 |
| | e | 0.15 | 0.17 | 0.23 | 0.22 | 7.30 | 9.59 | 9.85 | 10.19 | 8.4 | 17.6 | 17.9 | 20.9 | 6.27808 | 12.2794 | 17.5263 | 17.9416 |
| A Samples w/0.5% surfynol + 3%NaHCO3 | a | 0.18 | 0.23 | 0.20 | 0.18 | 7.30 | 9.99 | 9.52 | 9.95 | 7.7 | 16.7 | 16.4 | 18.9 | 7.5337 | 18.028 | 14.2362 | 13.9961 |
| | b | 0.18 | 0.23 | 0.19 | 0.21 | 7.30 | 9.89 | 9.00 | 9.76 | 7.6 | 14.5 | 15 | 18.3 | 7.5337 | 17.6689 | 12.0873 | 15.7112 |
| | c | 0.18 | 0.24 | 0.17 | 0.21 | 7.30 | 9.93 | 9.90 | 10.05 | 8.1 | 18.5 | 19.6 | 21.1 | 7.5337 | 18.5866 | 13.0861 | 16.6587 |
| | d | 0.18 | 0.23 | 0.23 | 0.22 | 7.30 | 9.93 | 9.55 | 9.68 | 8 | 18.6 | 19.2 | 20.3 | 7.5337 | 17.8121 | 16.475 | 16.1906 |
| | e | 0.18 | 0.20 | 0.20 | 0.19 | 7.30 | 9.60 | 9.43 | 9.77 | 7.5 | 18.1 | 15.2 | 19.6 | 7.5337 | 14.4765 | 13.9683 | 14.244 |
| A Samples w/3% NaHCO3 | a | 0.18 | 0.23 | 0.22 | 0.24 | 7.30 | 9.47 | 9.91 | 10.25 | 8.1 | 18.6 | 19 | 20.6 | 7.5337 | 16.2001 | 16.9691 | 19.8038 |
| | b | 0.18 | 0.20 | 0.22 | 0.22 | 7.30 | 9.45 | 10.23 | 9.90 | 7.9 | 18.5 | 19.4 | 20.1 | 7.5337 | 14.0276 | 18.0827 | 16.9349 |
| | c | 0.18 | 0.23 | 0.24 | 0.23 | 7.30 | 9.47 | 9.91 | 10.32 | 7.9 | 18.6 | 19 | 19.7 | 7.5337 | 16.2001 | 18.5118 | 19.2388 |
| | d | 0.19 | 0.25 | 0.25 | 0.19 | 7.30 | 9.52 | 9.88 | 10.22 | 8.1 | 19.2 | 20.3 | 21.2 | 7.95223 | 17.7952 | 19.1665 | 15.5864 |
| | e | 0.18 | 0.23 | 0.23 | 0.21 | 7.30 | 9.56 | 10.41 | 10.06 | 7.7 | 18.3 | 18.5 | 19 | 7.5337 | 16.5095 | 19.5758 | 16.6919 |
| H Samples | a | 0.41 | 0.49 | 0.49 | 0.51 | 7.30 | 8.66 | 8.59 | 8.98 | 17.6 | 29.8 | 30.3 | 31.4 | 17.1601 | 28.8617 | 25.6182 | 32.3008 |
| | b | 0.38 | 0.44 | 0.42 | 0.40 | 7.30 | 8.61 | 8.84 | 8.65 | 16.1 | 28.2 | 27.9 | 27.8 | 15.9045 | 25.6182 | 25.7777 | 23.5062 |
| | c | 0.43 | 0.56 | 0.48 | 0.51 | 7.30 | 8.38 | 8.71 | 8.69 | 17.7 | 30.6 | 30.9 | 31.4 | 17.9972 | 30.8863 | 28.6001 | 30.2482 |
| H Samples w/0.5%surfynol | d | 0.43 | 0.46 | 0.45 | 0.54 | 7.30 | 8.61 | 8.66 | 8.85 | 16.7 | 29.1 | 29.9 | 29.6 | 17.9972 | 26.7827 | 26.5056 | 33.2177 |
| | e | 0.38 | 0.41 | 0.42 | 0.49 | 7.30 | 8.65 | 8.57 | 8.55 | 15.9 | 28.1 | 26.9 | 29.1 | 15.9045 | 24.0938 | 24.2271 | 28.1331 |

FIGURE 1

Percent Change Compared to time 0

| | time (hrs) | thickness | | | | diameter | | | | weight | | | | volume | | | |
|---|---|---|---|---|---|---|---|---|---|---|---|---|---|---|---|---|---|
| | | 0 | 4 | 26 | 96 | 0 | 4 | 26 | 96 | 0 | 4 | 26 | 96 | 0 | 4 | 26 | 96 |
| A Samples w/0.5% surfanol | a | 0 | 20 | 0 | 20 | 0 | 25 | 35 | 34 | 0 | 114 | 109 | 116 | 0 | 87 | 81 | 117 |
| | b | 0 | 5 | 26 | 0 | 0 | 28 | 33 | 34 | 0 | 122 | 114 | 130 | 0 | 72 | 125 | 79.8538 |
| | c | 0 | 12 | 18 | 47 | 0 | 28 | 33 | 36 | 0 | 130 | 133 | 140 | 0 | 82 | 109 | 172.11 |
| | d | 0 | 24 | 12 | 6 | 0 | 31 | 33 | 37 | 0 | 123 | 129 | 122 | 0 | 112 | 97 | 98.6908 |
| | e | 0 | 33 | 28 | 22 | 0 | 31 | 29 | 34 | 0 | 142 | 143 | 156 | 0 | 128 | 113 | 119.372 |
| A Samples w/0.5% DSP | a | 0 | -10 | 35 | 30 | 0 | 28 | 34 | 37 | 0 | 128 | 124 | 132 | 0 | 47 | 142 | 145.414 |
| | b | 0 | -6 | 6 | 18 | 0 | 29 | 38 | 37 | 0 | 131 | 128 | 107 | 0 | 57 | 100 | 121.652 |
| | c | 0 | 7 | 33 | 13 | 0 | 32 | 35 | 39 | 0 | 134 | 134 | 139 | 0 | 86 | 142 | 119.101 |
| | d | 0 | -12 | 29 | 12 | 0 | 33 | 40 | 32 | 0 | 118 | 113 |  | 0 | 56 | 154 | 94.9005 |
| | e | 0 | -10 | 19 | 0 | 0 | 30 | 39 | 37 | 0 | 130 | 138 | 134 | 0 | 54 | 130 | 86.5282 |
| A Samples w/9% NaHCO3 | a | 0 | 6 | 29 | 82 | 0 | 27 | 35 | 39 | 0 | 110 | 122 | 141 | 0 | 71 | 135 | 250.452 |
| | b | 0 | 27 | 40 | 53 | 0 | 32 | 29 | 38 | 0 | 114 | 119 | 140 | 0 | 122 | 133 | 191.776 |
| | c | 0 | -16 | 37 | 21 | 0 | 34 | 35 | 38 | 0 | 114 | 115 | 138 | 0 | 52 | 148 | 131.724 |
| | d | 0 | 19 | 31 | 38 | 0 | 32 | 31 | 38 | 0 | 113 | 115 | 147 | 0 | 108 | 124 | 160.609 |
| | e | 0 | 13 | 53 | 47 | 0 | 31 | 35 | 40 | 0 | 110 | 113 | 149 | 0 | 96 | 179 | 185.781 |
| A Samples w/0.5% surfanol + 3%NaHCO3 | a | 0 | 28 | 11 | 0 | 0 | 37 | 30 | 36 | 0 | 117 | 113 | 145 | 0 | 139 | 89 | 86 |
| | b | 0 | 28 | 6 | 17 | 0 | 35 | 23 | 34 | 0 | 91 | 97 | 141 | 0 | 135 | 60 | 108.545 |
| | c | 0 | 33 | -6 | 17 | 0 | 36 | 36 | 38 | 0 | 128 | 142 | 160 | 0 | 147 | 74 | 121.123 |
| | d | 0 | 28 | 28 | 22 | 0 | 36 | 31 | 33 | 0 | 133 | 140 | 154 | 0 | 136 | 119 | 114.909 |
| | e | 0 | 11 | 11 | 6 | 0 | 32 | 29 | 34 | 0 | 141 | 103 | 161 | 0 | 92 | 85 | 89.0708 |
| A Samples w/3% NaHCO3 | a | 0 | 28 | 22 | 33 | 0 | 30 | 36 | 40 | 0 | 130 | 135 | 154 | 0 | 115 | 125 | 162.87 |
| | b | 0 | 11 | 22 | 22 | 0 | 29 | 40 | 36 | 0 | 134 | 146 | 154 | 0 | 86 | 140 | 124.789 |
| | c | 0 | 28 | 33 | 28 | 0 | 30 | 36 | 41 | 0 | 135 | 141 | 149 | 0 | 115 | 146 | 155.369 |
| | d | 0 | 32 | 32 | 0 | 0 | 30 | 35 | 40 | 0 | 137 | 151 | 162 | 0 | 124 | 141 | 96 |
| | e | 0 | 28 | 28 | 17 | 0 | 31 | 43 | 38 | 0 | 138 | 140 | 147 | 0 | 119 | 160 | 121.563 |
| H Samples w/0.5%surfynol | a | 0 | 20 | 20 | 24 | 0 | 19 | 18 | 23 | 0 | 69 | 72 | 78 | 0 | 68 | 65 | 88.2319 |
| | b | 0 | 16 | 11 | 5 | 0 | 18 | 21 | 18 | 0 | 75 | 73 | 73 | 0 | 61 | 62 | 47.7961 |
| | c | 0 | 30 | 12 | 19 | 0 | 15 | 19 | 19 | 0 | 73 | 75 | 77 | 0 | 72 | 59 | 68.0721 |
| | d | 0 | 7 | 5 | 26 | 0 | 18 | 19 | 21 | 0 | 74 | 79 | 77 | 0 | 49 | 47 | 84.5721 |
| | e | 0 | 8 | 11 | 29 | 0 | 18 | 17 | 17 | 0 | 77 | 69 | 83 | 0 | 51 | 52 | 76.8883 |

FIGURE 2

| Samples | | | Thickness % Change | | | Diameter % Change | | | Weight % Change | | | Volume % Change | | |
|---|---|---|---|---|---|---|---|---|---|---|---|---|---|---|
| | | | 4 hr | 26 hr | 96 hr | 4 hr | 26 hr | 96 hr | 4 hr | 26 hr | 96 hr | 4 hr | 26 hr | 96 hr |
| A | w/0.5% surfynol | ave | 19 | 17 | 19 | 28 | 33 | 35 | 126 | 126 | 133 | 96 | 105 | 117 |
| A | w/0.5% DSP | ave | -6 | 25 | 15 | 30 | 37 | 36 | 128 | 128 | 128 | 60 | 134 | 114 |
| A | w/9% NaHCO3 | ave | 10 | 38 | 48 | 32 | 33 | 38 | 112 | 117 | 143 | 90 | 144 | 184 |
| A | w/0.5% surfynol + 3%NaHCO3 | ave | 26 | 10 | 12 | 35 | 30 | 35 | 122 | 119 | 152 | 130 | 85 | 104 |
| A | w/3% NaHCO3 | ave | 25 | 27 | 20 | 30 | 38 | 39 | 135 | 142 | 153 | 112 | 142 | 132 |
| H | w/0.5%surfynol | ave | 16 | 11 | 21 | 18 | 19 | 20 | 74 | 74 | 78 | 60 | 57 | 73 |

FIGURE 3

In buffer pH= 7.2

| Samples | time (hrs) | thickness (mm) | | | | | | diameter (mm) | | | | | | weight (mg) | | | | | | volume (mm^3) | | | | | |
|---|---|---|---|---|---|---|---|---|---|---|---|---|---|---|---|---|---|---|---|---|---|---|---|---|---|
| | | 0 | 4.5 | 26 | 48 | 122 | | 0 | 4.5 | 26 | 48 | 122 | | 0 | 4.5 | 26 | 48 | 122 | | 0 | 4.5 | 26 | 48 | 122 | |
| A | A1 | 0.19 | 0.31 | 0.44 | 0.28 | 0.29 | | 7.30 | 9.80 | 9.28 | 9.85 | 9.76 | | 13.5 | 27.8 | 29.1 | 28.8 | 36.1 | | 7.95223 | 23.3832 | 29.7604 | 21.3364 | 21.6964 | 0 |
| | A2 | 0.21 | 0.36 | 0.29 | 0.28 | 0.31 | | 7.30 | 9.49 | 9.75 | 9.82 | 9.97 | | 12.6 | 28.6 | 27.3 | 26.5 | 23.5 | | 8.78931 | 25.4639 | 21.652 | 21.2066 | 24.2015 | 0 |
| | A3 | 0.23 | 0.27 | 0.37 | 0.24 | 0.41 | | 7.30 | 9.85 | 9.38 | 9.65 | 9.81 | | 12.5 | 27.2 | 28.1 | 26.6 | 27.3 | | 9.62639 | 20.5743 | 25.568 | 17.5532 | 30.9893 | 0 |
| | A4 | 0.14 | 0.23 | 0.23 | 0.16 | 0.22 | | 7.30 | 10.18 | 9.82 | 10.29 | 10.24 | | 10.1 | 22 | 22.1 | 23 | 20.4 | | 5.85954 | 18.7203 | 17.4197 | 13.3058 | 18.1181 | 0 |
| | A5 | 0.22 | 0.33 | 0.31 | 0.26 | 0.38 | | 7.30 | 9.79 | 9.86 | 9.76 | 10.67 | | 12.5 | 28.9 | 29.1 | 27.8 | 30 | | 9.20785 | 24.841 | 23.6704 | 19.4519 | 33.9784 | 0 |
| A | B1 | 1.15 | 1.40 | 1.53 | 1.30 | 1.37 | | 7.30 | 9.15 | 9.39 | 9.47 | 9.37 | | 52.4 | 108.1 | 109.9 | 111 | 119.2 | | 48.1319 | 92.0577 | 105.953 | 91.5658 | 94.4691 | 0 |
| | B2 | 0.99 | 1.31 | 1.35 | 1.28 | 1.23 | | 7.30 | 9.97 | 9.38 | 9.53 | 10.00 | | 48.5 | 96.4 | 103.9 | 105.5 | 111.7 | | 41.4353 | 102.271 | 93.2888 | 91.3031 | 96.604 | 0 |
| | B3 | 0.64 | 0.87 | 0.84 | 0.86 | 0.85 | | 7.30 | 9.52 | 9.67 | 9.43 | 10.17 | | 34 | 72 | 74.4 | 74.3 | 79.9 | | 26.7865 | 61.9274 | 61.691 | 60.0636 | 69.0479 | 0 |
| | B4 | 0.57 | 0.89 | 1.16 | 0.66 | 0.82 | | 7.30 | 9.38 | 9.48 | 9.27 | 10.22 | | 28.3 | 61.6 | 64 | 62.7 | 66.1 | | 23.8567 | 61.5015 | 81.8775 | 44.5444 | 67.2675 | 0 |
| | B5 | 0.52 | 0.74 | 0.73 | 0.70 | 0.86 | | 7.30 | 9.35 | 9.79 | 9.57 | 9.87 | | 29 | 60.2 | 65.8 | 65.1 | 71.8 | | 21.764 | 50.8095 | 54.9513 | 50.3514 | 65.7995 | 0 |
| A | C1 | 4.59 | 6.92 | 7.21 | 6.35 | 7.73 | | 7.30 | 9.05 | 9.09 | 9.49 | 9.45 | | 77 | 186.4 | 193.9 | 187.6 | 195.2 | | 192.109 | 445.136 | 467.9 | 449.155 | 542.167 | 0 |
| | C2 | 3.40 | 5.21 | 5.14 | 4.96 | 5.16 | | 7.30 | 9.40 | 9.10 | 9.40 | 9.56 | | 67.4 | 166.7 | 173.8 | 176.8 | 187.7 | | 142.303 | 361.562 | 334.3 | 344.213 | 370.387 | 0 |
| | C3 | 3.03 | 3.58 | 4.33 | 4.73 | 4.71 | | 7.30 | 8.49 | 9.10 | 9.52 | 9.52 | | 60.5 | 148.4 | 146.7 | 151.7 | 154.6 | | 126.817 | 202.669 | 281.618 | 336.686 | 335.262 | 0 |
| | C4 | 3.64 | 5.29 | 5.46 | 4.90 | 5.41 | | 7.30 | 8.85 | 8.98 | 8.52 | 8.92 | | 63.4 | 154.4 | 163.8 | 160.1 | 171.4 | | 152.348 | 325.411 | 345.808 | 279.361 | 338.078 | 0 |
| | C5 | 3.29 | 4.25 | 4.15 | 3.39 | 4.78 | | 7.30 | 8.26 | 9.22 | 9.33 | 9.25 | | 64.3 | 164.5 | 149 | 160.6 | 178.1 | | 137.699 | 227.74 | 277.077 | 231.768 | 321.219 | 0 |

FIGURE 4

Thickness
A average=0.2mm
B average=0.77mm
C average=3.59mm

Percent change compared to time 0

| Samples | time (hrs) | thickness | | | | | diameter | | | | | weight | | | | | volume | | | | |
|---|---|---|---|---|---|---|---|---|---|---|---|---|---|---|---|---|---|---|---|---|---|
| | | 0 | 4.5 | 26 | 48 | 122 | 0 | 4.5 | 26 | 48 | 122 | 0 | 4.5 | 26 | 48 | 122 | 0 | 4.5 | 26 | 48 | 122 |
| A | A1 | 0 | 63 | 132 | 47 | 53 | 0 | 34 | 27 | 35 | 34 | 0 | 106 | 116 | 113 | 167 | 0 | 194 | 274 | 168 | 122 |
| | A2 | 0 | 71 | 38 | 33 | 48 | 0 | 30 | 34 | 35 | 37 | 0 | 127 | 117 | 110 | 87 | 0 | 190 | 146 | 141 | 173 |
| | A3 | 0 | 17 | 61 | 4 | 78 | 0 | 35 | 28 | 32 | 34 | 0 | 118 | 125 | 113 | 118 | 0 | 114 | 166 | 82 | 175 |
| | A4 | 0 | 64 | 64 | 14 | 57 | 0 | 39 | 35 | 41 | 40 | 0 | 118 | 119 | 128 | 102 | 0 | 219 | 197 | 127 | 222 |
| | A5 | 0 | 50 | 41 | 18 | 73 | 0 | 34 | 35 | 34 | 46 | 0 | 131 | 133 | 122 | 140 | 0 | 170 | 157 | 111 | 209 |
| A | B1 | 0 | 22 | 33 | 13 | 19 | 0 | 25 | 29 | 30 | 28 | 0 | 106 | 110 | 112 | 127 | 0 | 91 | 120 | 90 | 269 |
| | B2 | 0 | 32 | 36 | 29 | 24 | 0 | 37 | 28 | 31 | 37 | 0 | 99 | 114 | 118 | 130 | 0 | 147 | 125 | 120 | 96 |
| | B3 | 0 | 36 | 31 | 34 | 33 | 0 | 30 | 32 | 29 | 39 | 0 | 112 | 119 | 119 | 135 | 0 | 131 | 130 | 124 | 133 |
| | B4 | 0 | 56 | 104 | 16 | 44 | 0 | 28 | 30 | 27 | 40 | 0 | 118 | 126 | 122 | 134 | 0 | 158 | 243 | 87 | 158 |
| | B5 | 0 | 42 | 40 | 35 | 65 | 0 | 28 | 34 | 31 | 35 | 0 | 108 | 127 | 124 | 148 | 0 | 133 | 152 | 131 | 182 |
| A | C1 | 0 | 51 | 57 | 38 | 68 | 0 | 24 | 25 | 30 | 29 | 0 | 142 | 152 | 144 | 154 | 0 | 132 | 144 | 134 | 202 |
| | C2 | 0 | 53 | 51 | 46 | 52 | 0 | 29 | 25 | 29 | 31 | 0 | 147 | 156 | 162 | 178 | 0 | 154 | 135 | 142 | 182 |
| | C3 | 0 | 18 | 43 | 56 | 55 | 0 | 16 | 25 | 30 | 30 | 0 | 145 | 142 | 151 | 156 | 0 | 60 | 122 | 165 | 160 |
| | C4 | 0 | 45 | 50 | 35 | 49 | 0 | 21 | 23 | 17 | 22 | 0 | 144 | 158 | 153 | 170 | 0 | 114 | 127 | 83 | 164 |
| | C5 | 0 | 29 | 26 | 3 | 45 | 0 | 13 | 26 | 28 | 27 | 0 | 156 | 132 | 150 | 177 | 0 | 65 | 101 | 68 | 122 |

FIGURE 5

Percent change compared to time 0

| Samples | time (h) | thickness | | | | diameter | | | | weight | | | | volume | | | |
|---|---|---|---|---|---|---|---|---|---|---|---|---|---|---|---|---|---|
| | | 0 | 4.5 | 26 | 48 | 122 | 0 | 4.5 | 26 | 48 | 122 | 0 | 4.5 | 26 | 48 | 122 | 0 | 4.5 | 26 | 48 | 122 |
| A | A av | | 53 | 67 | 24 | 62 | | 35 | 32 | 35 | 38 | | 120 | 122 | 117 | 123 | | 177 | 188 | 126 | 210 |
| | B av | | 38 | 49 | 25 | 37 | | 30 | 31 | 30 | 36 | | 108 | 119 | 119 | 135 | | 132 | 154 | 111 | 154 |
| | C av | | 39 | 45 | 36 | 54 | | 21 | 25 | 27 | 28 | | 147 | 148 | 152 | 167 | | 105 | 126 | 119 | 152 |

A average= 0.2 mm; B average= 0.77 mm; C average= 3.6 mm

FIGURE 6

In buffer pH= 7.2

| Samples | time (h) | thickness (mm) 0 | 4 | 26 | 4 days | diameter (mm) 0 | 4 | 26 | 4 days | weight (mg) 0 | 4 | 26 | 4 days | volume (mm^3) 0 | 4 | 26 | 4 days |
|---|---|---|---|---|---|---|---|---|---|---|---|---|---|---|---|---|---|
| A | a | 0.19 | 0.31 | 0.44 | | 7.30 | 9.80 | 9.28 | | 13.5 | 27.8 | 29.1 | | 7.9522 | 23.383 | 29.76 | 29.194 |
|  | b | 0.21 | 0.36 | 0.29 | | 7.30 | 9.49 | 9.75 | | 12.6 | 28.6 | 27.3 | | 8.7893 | 25.464 | 21.652 | 46.939 |
|  | c | 0.23 | 0.27 | 0.37 | | 7.30 | 9.85 | 9.38 | | 12.5 | 27.2 | 28.1 | | 9.6264 | 20.574 | 25.568 | 27.432 |
|  | d | 0.14 | 0.23 | 0.23 | | 7.30 | 10.18 | 9.82 | | 10.1 | 22 | 22.1 | | 5.8595 | 18.72 | 17.42 | 25.564 |
|  | e | 0.22 | 0.33 | 0.31 | | 7.30 | 9.79 | 9.86 | | 12.5 | 28.9 | 29.1 | | 9.2079 | 24.841 | 23.67 | 40.381 |
| D | a | 0.31 | 0.37 | 0.32 | | 7.30 | 9.54 | 9.38 | | 12.3 | 25.2 | 24.8 | | 12.975 | 26.448 | 22.113 | |
|  | b | 0.20 | 0.19 | 0.21 | | 7.30 | 9.68 | 9.27 | | 7.1 | 14.5 | 14.1 | | 8.3708 | 13.983 | 14.173 | |
|  | c | 0.22 | 0.25 | 0.24 | | 7.30 | 9.93 | 9.59 | | 8.2 | 18 | 18.2 | | 9.2079 | 19.361 | 17.336 | |
|  | d | 0.18 | 0.20 | 0.18 | | 7.30 | 9.11 | 9.92 | | 7.2 | 14.6 | 16 | | 7.5337 | 13.036 | 13.912 | |
|  | e | 0.20 | 0.21 | 0.20 | | 7.30 | 9.32 | 9.88 | | 7.5 | 15.6 | 17.4 | | 8.3708 | 14.327 | 15.333 | |
| E | a | 0.27 | 0.28 | 0.29 | | 7.30 | 8.43 | 8.78 | | 11.1 | 16.8 | 17.2 | | 11.301 | 15.628 | 17.558 | |
|  | b | 0.28 | 0.31 | 0.30 | | 7.30 | 9.04 | 8.74 | | 11.1 | 17.5 | 18.8 | | 11.719 | 19.897 | 17.998 | |
|  | c | 0.35 | 0.41 | 0.41 | | 7.30 | 8.48 | 8.65 | | 16 | 24.6 | 26.4 | | 14.649 | 23.156 | 24.094 | |
|  | d | 0.29 | 0.33 | 0.30 | | 7.30 | 8.52 | 8.81 | | 12.5 | 18.8 | 20.7 | | 12.138 | 18.814 | 18.288 | |
|  | e | 0.35 | 0.40 | 0.41 | | 7.30 | 8.62 | 9.06 | | 13.1 | 21 | 21.6 | | 14.649 | 23.343 | 26.432 | |
| F | a | 0.36 | 0.43 | 0.42 | | 7.30 | 9.1 | 9.05 | | 17.3 | 32.3 | 31.7 | | 15.067 | 27.967 | 27.017 | |
|  | b | 0.36 | 0.43 | 0.45 | | 7.30 | 9.6 | 8.91 | | 17.9 | 35.4 | 34.5 | | 15.067 | 31.124 | 28.058 | |
|  | c | 0.36 | 0.44 | 0.43 | | 7.30 | 9.53 | 8.85 | | 17.6 | 34.4 | 31.5 | | 15.067 | 31.385 | 26.451 | |
|  | d | 0.35 | 0.46 | 0.45 | | 7.30 | 9.41 | 8.99 | | 17.7 | 34.3 | 34.2 | | 14.649 | 31.991 | 28.564 | |
|  | e | 0.38 | 0.48 | 0.48 | | 7.30 | 9.33 | 8.95 | | 18.8 | 36.6 | 36.6 | | 15.904 | 32.817 | 30.198 | |
| G | a | 0.20 | 0.26 | 0.25 | | 7.30 | 10.77 | 10.75 | | 9.2 | 23.4 | 24.9 | | 8.3708 | 23.686 | 22.691 | |
|  | b | 0.15 | 0.21 | 0.19 | | 7.30 | 10.64 | 10.54 | | 7.6 | 16.4 | 19.8 | | 6.2781 | 18.672 | 16.578 | |
|  | c | 0.16 | 0.27 | 0.22 | | 7.30 | 10.62 | 10.91 | | 8.2 | 20.9 | 21.7 | | 6.6966 | 23.917 | 20.567 | |
|  | d | 0.15 | 0.23 | 0.20 | | 7.30 | 10.65 | 10.79 | | 7.6 | 19.7 | 20.8 | | 6.2781 | 20.489 | 18.288 | |
|  | e | 0.16 | 0.22 | 0.21 | | 7.30 | 10.82 | 10.92 | | 7.7 | 19.3 | 20.3 | | 6.6966 | 20.229 | 19.668 | |
| H | a | 0.40 | 0.43 | 0.46 | 0.48 | 7.30 | 8.75 | 8.62 | 8.80 | 19.9 | 33.8 | 34.3 | 34.9 | 16.742 | 25.857 | 26.845 | |
|  | b | 0.54 | 0.75 | 0.66 | 0.77 | 7.30 | 8.61 | 8.31 | 8.81 | 28.6 | 48.5 | 50.1 | 50.9 | 22.601 | 43.667 | 35.796 | |
|  | c | 0.39 | 0.44 | 0.45 | 0.45 | 7.30 | 8.90 | 9.24 | 8.81 | 19.1 | 32.6 | 33.9 | 34.1 | 16.323 | 27.373 | 30.175 | |
|  | d | 0.37 | 0.46 | 0.42 | 0.41 | 7.30 | 8.88 | 8.85 | 8.91 | 18.6 | 32.7 | 32.2 | 33 | 15.486 | 28.489 | 25.836 | |
|  | e | 0.52 | 0.66 | 0.58 | 0.67 | 7.30 | 8.82 | 8.63 | 8.76 | 26.1 | 43.1 | 44.2 | 47.4 | 21.764 | 40.325 | 33.927 | |

FIGURE 9

| Samples | time (h) | Percent Change Compared to week 0 | | | | | | | | | | | |
|---|---|---|---|---|---|---|---|---|---|---|---|---|---|
| | | thickness | | | diameter | | | weight | | | volume | | |
| | | 0 | 4 | 26 | 4 days | 0 | 4 | 26 | 4 days | 0 | 4 | 26 | 4 days | 0 | 4 | 26 | 4 days |

| Samples | time (h) | thickness 0 | thickness 4 | thickness 26 | thickness 4 days | diameter 0 | diameter 4 | diameter 26 | diameter 4 days | weight 0 | weight 4 | weight 26 | weight 4 days | volume 0 | volume 4 | volume 26 | volume 4 days |
|---|---|---|---|---|---|---|---|---|---|---|---|---|---|---|---|---|---|
| A | a | 0 | 63 | 132 | | 0 | 34 | 27 | | 0 | 106 | 116 | | 0 | 194 | 274 | |
| A | b | 0 | 71 | 38 | | 0 | 30 | 34 | | 0 | 127 | 117 | | 0 | 190 | 146 | |
| A | c | 0 | 17 | 61 | | 0 | 35 | 28 | | 0 | 118 | 125 | | 0 | 114 | 166 | |
| A | d | 0 | 64 | 64 | | 0 | 39 | 35 | | 0 | 118 | 119 | | 0 | 219 | 197 | |
| A | e | 0 | 50 | 41 | | 0 | 34 | 35 | | 0 | 131 | 133 | | 0 | 170 | 157 | |
| D | a | 0 | 19 | 3 | | 0 | 31 | 28 | | 0 | 105 | 102 | | 0 | 104 | 70 | |
| D | b | 0 | -5 | 5 | | 0 | 33 | 27 | | 0 | 104 | 99 | | 0 | 67 | 69 | |
| D | c | 0 | 14 | 9 | | 0 | 36 | 31 | | 0 | 120 | 122 | | 0 | 110 | 88 | |
| D | d | 0 | 11 | 0 | | 0 | 25 | 36 | | 0 | 103 | 122 | | 0 | 73 | 85 | |
| D | e | 0 | 5 | 0 | | 0 | 28 | 35 | | 0 | 108 | 132 | | 0 | 71 | 83 | |
| E | a | 0 | 4 | 7 | | 0 | 15 | 20 | | 0 | 51 | 55 | | 0 | 38 | 55 | |
| E | b | 0 | 11 | 7 | | 0 | 24 | 20 | | 0 | 58 | 69 | | 0 | 70 | 54 | |
| E | c | 0 | 17 | 17 | | 0 | 16 | 18 | | 0 | 54 | 65 | | 0 | 58 | 64 | |
| E | d | 0 | 14 | 3 | | 0 | 17 | 21 | | 0 | 50 | 66 | | 0 | 55 | 51 | |
| E | e | 0 | 14 | 17 | | 0 | 18 | 24 | | 0 | 60 | 65 | | 0 | 59 | 80 | |
| F | a | 0 | 19 | 17 | | 0 | 25 | 24 | | 0 | 87 | 83 | | 0 | 86 | 79 | |
| F | b | 0 | 19 | 25 | | 0 | 32 | 22 | | 0 | 98 | 93 | | 0 | 107 | 86 | |
| F | c | 0 | 22 | 19 | | 0 | 31 | 21 | | 0 | 95 | 79 | | 0 | 108 | 76 | |
| F | d | 0 | 31 | 29 | | 0 | 29 | 23 | | 0 | 94 | 93 | | 0 | 118 | 95 | |
| F | e | 0 | 26 | 26 | | 0 | 28 | 23 | | 0 | 95 | 95 | | 0 | 106 | 90 | |
| G | a | 0 | 30 | 25 | | 0 | 48 | 47 | | 0 | 154 | 171 | | 0 | 183 | 171 | |
| G | b | 0 | 40 | 27 | | 0 | 46 | 44 | | 0 | 116 | 161 | | 0 | 197 | 164 | |
| G | c | 0 | 69 | 38 | | 0 | 45 | 49 | | 0 | 155 | 165 | | 0 | 257 | 207 | |
| G | d | 0 | 53 | 33 | | 0 | 46 | 48 | | 0 | 159 | 174 | | 0 | 226 | 191 | |
| G | e | 0 | 38 | 31 | | 0 | 48 | 50 | | 0 | 151 | 164 | | 0 | 202 | 194 | |
| H | a | 0 | 7 | 15 | 20 | 0 | 20 | 18 | 21 | 0 | 70 | 72 | 75 | 0 | 54 | 60 | 74.3817 |
| H | b | 0 | 39 | 22 | 43 | 0 | 18 | 14 | 21 | 0 | 70 | 75 | 78 | 0 | 93 | 58 | 107.684 |
| H | c | 0 | 13 | 15 | 15 | 0 | 22 | 27 | 22 | 0 | 71 | 77 | 79 | 0 | 68 | 85 | 68.056 |
| H | d | 0 | 24 | 14 | 11 | 0 | 22 | 21 | 22 | 0 | 76 | 73 | 77 | 0 | 84 | 67 | 65.079 |
| H | e | 0 | 27 | 12 | 29 | 0 | 21 | 18 | 20 | 0 | 65 | 69 | 82 | 0 | 85 | 56 | 85.5385 |
| A | ave | | 53 | 67 | | | 35 | 32 | | | 120 | 122 | | | 177 | 188 | |
| D | ave | | 9 | 3 | | | 30 | 32 | | | 108 | 115 | | | 85 | 79 | |
| E | ave | | 12 | 10 | | | 18 | 21 | | | 55 | 64 | | | 56 | 61 | |
| F | ave | | 24 | 23 | | | 29 | 23 | | | 94 | 89 | | | 105 | 85 | |
| G | ave | | 46 | 31 | | | 47 | 48 | | | 147 | 167 | | | 213 | 185 | |
| H | ave | | 22 | 16 | 24 | | 20 | 20 | 21 | | 70 | 73 | 78 | | 77 | 65 | 80.1478 |

FOAM CONTROL FOR SYNTHETIC ADHESIVE/SEALANT

TECHNICAL FIELD

The present disclosure relates to methods for producing biocompatible polymers capable of forming a matrix and the use of these polymers as surgical adhesives or sealants.

DESCRIPTION OF THE RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, in embodiments a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high flexural modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

The development of synthetic biocompatible adhesives and/or sealants is ongoing. An advantage of these materials over the natural materials described above is their consistency and reduced risk of viral transmission. Some current adhesives and/or sealants include those based upon polyurethane matrices. In some cases, foaming or bubbling may occur in the formation of these matrices. One potential concern with the formation of foam and/or bubbles is that the bubbles may become trapped in the resulting matrix, resulting in the formation of dispersed defects, i.e., points of weakness, in the matrix. Such defects may also reduce the cohesive and/or adhesive strength of the resulting matrix.

It would thus be desirable to develop improved methods to produce synthetic biological adhesives and/or sealants to minimize the formation of these potential defects and maximize the physical properties of the resulting adhesives and/or sealants.

SUMMARY

The present disclosure provides polymeric compositions suitable for use as surgical adhesives and/or sealants, and the use of foam control agents in these compositions. Methods for forming these compositions are also provided. In embodiments, methods of the present disclosure include contacting at least one isocyanate-functional polyurethane prepolymer with at least one foam control agent, applying the at least one isocyanate-functional polyurethane prepolymer with at least one foam control agent to tissue, and allowing the at least one isocyanate-functional polyurethane prepolymer to react with the tissue, wherein the at least one isocyanate-functional polyurethane prepolymer crosslinks upon contact with water in the tissue thereby forming a biocompatible composition possessing a strength profile that is not compromised by the presence of the foam control agent.

In embodiments, the at least one isocyanate-terminated prepolymer may be prepared by reacting a first polyol such as polyether polyols, polycaprolactone polyols, and polyhydric alcohols with a first polyisocyanate such as aromatic, aliphatic and alicyclic diisocyanates, to produce an isocyanate end-capped polyol, reacting the isocyanate end-capped polyol with a second polyol to produce a polyurethane, and reacting the polyurethane with a second polyisocyanate to produce the isocyanate-functional polyurethane prepolymer.

Biocompatible adhesives and sealants comprising these biocompatible compositions are also provided. Methods for closing wounds, filling voids in animal tissue, and adhering medical devices to a surface of animal tissue with these compositions are also provided.

BRIEF DESCRIPTION OF THE DRAWINGS

Various embodiments of the present disclosure will be described herein below with reference to the figures wherein:

FIG. 1 is a table of data showing thickness, diameter, weight, and volume of samples produced with compositions in accordance with the present disclosure;

FIG. 2 is a table of data showing the percent change in thickness, diameter, weight, and volume of samples from FIG. 1 over time;

FIG. 3 is a table of data showing the average percent change in thickness, diameter, weight, and volume of samples identified in FIG. 1 over time;

FIG. 4 is a table of data showing thickness, diameter, weight, and volume of additional samples produced with compositions in accordance with the present disclosure;

FIG. 5 is a table of data showing the percent change in thickness, diameter, weight, and volume of samples from FIG. 4 over time;

FIG. 6 is a table of data showing the average percent change in thickness, diameter, weight, and volume of samples identified in FIG. 4 over time;

FIG. 9 is a is a table of data showing thickness, diameter, weight, and volume of additional samples produced with compositions in accordance with the present disclosure; and FIG. 10 is a table of data showing the percent change in thickness, diameter, weight, and volume of samples from FIG. 9 over time.

DETAILED DESCRIPTION

Figure 8:
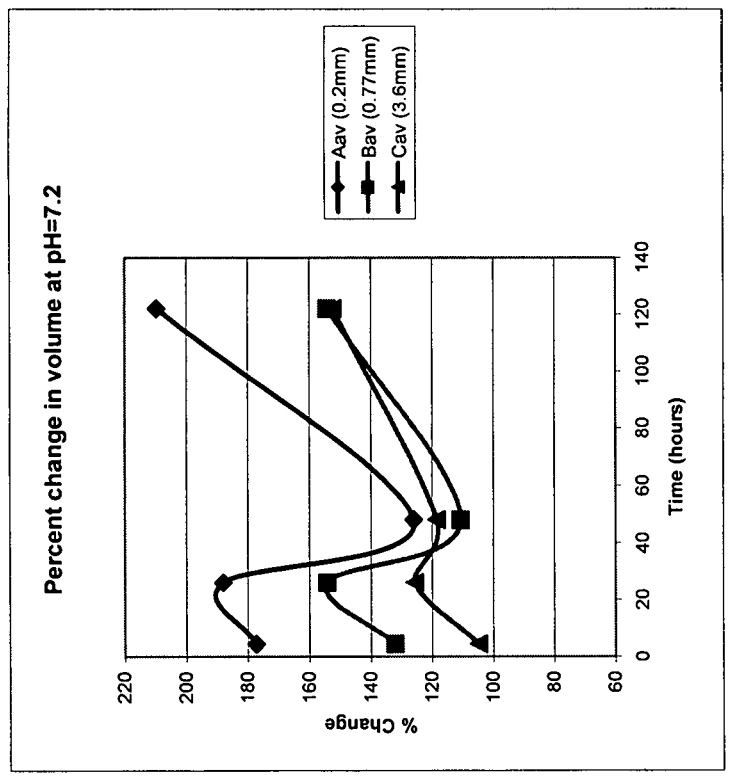
FIG. 8 is a graph depicting the average percent change in volume of the samples from FIG. 4 over time.

The present disclosure relates to methods for producing biocompatible compositions for use as tissue adhesives and/or sealants. The biocompatible compositions produced by these methods may be biocompatible and non-immunogenic. The biocompatible compositions can be employed to adhere tissue edges, seal air/fluid leaks in tissues, adhere medical devices, i.e. implants, to tissue, and for tissue augmentation such as sealing or filling voids or defects in tissue. The biocompatible compositions can be applied to living tissue and/or flesh of animals, including humans.

While certain distinctions may be drawn between the terms "flesh" and "tissue" within the scientific community, the terms are used interchangeably herein as referring to a general substrate upon which those skilled in the art would understand the present adhesive and/or sealant compositions to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic and/or ascite tissue.

The present disclosure includes combining a foam control agent with an isocyanate-functional polyurethane prepolymer to reduce the formation of bubbles and/or foam as the isocyanate-functional polyurethane prepolymer forms an adhesive or sealant of the present disclosure. As used herein, the terms "foam control agent", "defoamer", "defoaming agent" and/or "antifoaming agent" may be used interchangeably and include any agent or compound added to a prepolymer to destabilize and/or prevent the formation of bubbles or foam in an adhesive or sealant of the present disclosure. By eliminating the foam or controlling the size distribution of any bubbles in an adhesive and/or sealant of the present disclosure, the use of foam control agents as contemplated herein may significantly enhance the physical properties of an adhesive and/or sealant prepared therewith.

Suitable foam control agents which may be utilized in accordance with the present disclosure include, but are not limited to, hydrophobic component(s), optionally in combination with carrier vehicle(s) and/or emulsifier(s). Examples of suitable hydrophobic components include, but are not limited to, treated silica such as methylated silica and trimethylated silica, waxes such as lauryl palmitate and stearyl stearate, silicones including siloxanes such as polydialkylsiloxanes including polydimethyl siloxanes, cyclic siloxanes including cyclopentansiloxane, octamethyl cyclotetrasiloxane, decamethyl cyclopentasiloxane, dodecamethyl cyclohexasiloxane, dimethyl cyclosiloxanes, silicone derivatives such as trimethylsiloxysilicate, cetearyl methicone, dimethicone, dimethicone copolyol, cyclomethicone, simethicone, diols such as acetylenic diols, alkane diols, and tetramethyl dodecyne diols, combinations thereof, and the like. Where utilized in combination with other materials, the hydrophobic component may be the most surface-active component of the foam control agent.

In embodiments, a silicone foam control agent such as NuSil MED-340 (from NuSil Technology LLC, Carpinteria, Calif.), Dow Corning Medical Antifoam A Compound, Dow Corning Medical Antifoam C Emulsion, or DSP Emulsion (from Dow Corning Corporation, Midland, Mich.), may be utilized. In other embodiments, non-silicone foam control agents such as SURFYNOL® MD-20 defoamer (from Air Products and Chemicals, Inc., Allentown, Pa.), may be utilized. Such foam control agents may be extremely hydrophobic and thus incompatible with water. In some cases, such foam control agents may have a low surface tension from about 15 mN/m to about 25 mN/m, in embodiments about 20 mN/m, which renders them highly surface active.

In other embodiments non-silicone acetylenic diol based surfactants may be utilized as the hydrophobic component. Such surfactants may have a low molecular weight and a branching geometry, which may provide low dynamic surface tension desirable for excellent wetting and excellent foam control.

Where present, suitable carrier vehicles include, for example, mineral oils such as liquid paraffin and the distillation products obtained from mineral raw materials such as petroleum, lignite tar, coal tar, wood, and peat, which may be mixtures of saturated hydrocarbons, cyclic hydrocarbons, combinations thereof, and the like; vegetable oils such as almond oil, apricot kernel oil, avocado oil, castor oil, hydrogenated castor oil, coconut oil, hydrogenated coconut fatty glycerides, corn oil, evening primrose oil, jojoba oil, linseed oil, olive oil, palm oil, peanut oil, rapeseed oil, safflower oil, sesame oil, soybean oil, sunflower oil, wheat germ oil, cotton seed oil, palm kernel oil, combinations thereof, and the like; silicone oils such as polyalkyl siloxanes including polydimethyl siloxanes, cyclic dimethyl polysiloxanes such as cyclomethicone, cyclopentasiloxane, dimethiconols, combinations thereof, and the like; alcohols including ethanol, mannitol, sorbitol, glycerol, xylitol, polyols, combinations thereof, and the like; glycols including alkylene glycols such as propylene glycol, polypropylene glycol, ethylene glycol, polyethylene glycol, diethylene glycol, combinations thereof, and the like; water; combinations of the foregoing, and the like. Carrier vehicles may assist in homogeneously transferring the hydrophobic component into the matrix of the present disclosure as it forms an adhesive or sealant.

Suitable emulsifiers which may be utilized in accordance with the present disclosure include, for example, ethoxylated alkylphenols such as nonylphenol ethoxylate, sorbitan esters such as sorbitan tristearate, sorbitan sesquioleate, sorbitan monooleate, sorbitan laurate, sorbitan oleate, polyethylene glycol ethers such as polyethylene glycol stearyl ether, polyethylene glycol esters such as polyethylene glycol stearate, polyethylene glycol distearate, polyethylene glycol palmitostearate, polyethylene glycol dilaurate, polyethylene glycol dioleate, combinations thereof, and the like. The emulsifiers may assist in optimizing the distribution of the hydrophobic component in the carrier and the distribution of the foam control agent throughout the matrix to which they may be applied.

In embodiments, the foam control agent may be added to isocyanate-functional polyurethane prepolymers. As will be appreciated by one of skill in the art, the isocyanate terminal of isocyanate-functional polyurethane prepolymers will react with water upon application to tissue, thereby generating carbon dioxide and amine groups. The amine groups may internally react with other isocyanate terminal groups to form strong urea bonds while the carbon dioxide tries to escape from the forming polyurethane (due in part, to its low density). As the reaction continues, carbon dioxide gas bubbles continue to form while the viscosity of the polymer increases due, in part, to cross-linking. As a result, the carbon dioxide gas bubbles may become trapped inside the polymer resulting in foaming/bubble formation, which may result in dispersion of the gas bubbles throughout the polymer matrix. One potential concern with the formation of foam and/or bubbles is the bubbles may become trapped in the resulting matrix, resulting in the formation of dispersed defects, i.e., points of weakness, in the matrix. Such defects may also reduce the cohesive and adhesive strength of the resulting matrix as well as result in matrices having a low modulus and break strength. The addition of foam control agents as described herein may thus be utilized to form adhesives and/or sealants having desirable physical properties with reduced amounts of defects, and the foam control agents may reduce the formation of bubbles and/or foam in such adhesives and/or sealants.

While any biocompatible isocyanate-functional polyurethane prepolymer may be utilized to form an adhesive and/or sealant of the present disclosure, in embodiments the isocyanate-functional polyurethane prepolymers may be based upon biocompatible polyols. Such prepolymers are within the purview of those skilled in the art.

For example, in embodiments a first biocompatible polyol may be endcapped with a polyisocyanate; the resulting isocyanate-endcapped polyol may then be reacted with a second polyol to produce a polyurethane; and the resulting polyurethane may then be reacted with an additional polyisocyanate to produce an isocyanate-functional polyurethane prepolymer. Upon application to tissue, the isocyanate terminal of the isocyanate-functional polyurethane prepolymer may react with water in the tissue to thereby form an adhesive and/or sealant of the present disclosure.

Useful biocompatible polyols for use as the first polyol include polyether polyols, polycaprolactone polyols, and polyhydric alcohols such as glycerol, trimethylolpropane, hexane-1,2,6-triol, pentaerythritol, sorbitol, mannitol, polyalkylene oxides such as polyethylene glycols (PEGs), diethylene glycol, and poloxamers such as polyethylene oxide (PEO) copolymers with polypropylene oxide (PPO) such as the triblock PEO-PPO copolymers commercially available as PLURONICS® from BASF Corporation (Mt. Olive, N.J.). In embodiments, combinations of the foregoing may be utilized as the first polyol.

The molecular weight of the first polyol can vary depending upon the intended end use of the biocompatible composition, i.e., as an adhesive or sealant. In some embodiments, the molecular weight of the polyol can be from about 100 g/mol to about 10,000 g/mol, in embodiments from about 130 g/mol to about 2,000 g/mol. In some useful embodiments, the molecular weight of the polyol can be from about 200 g/mol to about 1,000 g/mol. Where the first polyol is a PEG, it may be desirable to utilize a PEG with a molecular weight of from about 200 to about 1000, in embodiments from about 400 to about 900. Suitable PEGs are commercially available from a variety of sources under the designations PEG 200, PEG 400, PEG 600 and PEG 900.

In embodiments, the first polyol may include the above polyalkylene oxides in combination with aliphatic dicarboxylic acids or their reactive derivatives. Suitable aliphatic dicarboxylic acids include those having from about 2 to about 10 carbon atoms such as sebacic acid, azelaic acid, suberic acid, pimelic acid, adipic acid, glutaric acid, succinic acid, malonic acid, oxalic acid, dodecanoic acid, and combinations thereof. Suitable derivatives of the aliphatic dicarboxylic acids include, for example, oxalyl chloride, malonyl chloride, succinyl chloride, glutaryl chloride, adipoyl chloride, adipoyl dichloride, suberoyl chloride, pimeloyl chloride, sebacoyl chloride, and/or combinations thereof. As used herein, an aliphatic dicarboxylic acid includes both the diacids and derivatives thereof described above.

The polyalkylene oxide and aliphatic dicarboxylic acid may be combined in any order. In some embodiments, the components may be combined at one time; in other embodiments the components may be combined over a period of time, for example by dropwise addition of one component to the other, from about 0.5 ml/minute to about 20 ml/minute, in embodiments from about 2 ml/minute to about 15 ml/minute.

In embodiments, it may be desirable to utilize mechanical agitation to assist in combining the polyalkylene oxide and aliphatic dicarboxylic acid. Any method within the purview of those skilled in the art may be utilized including, for example, blending, mixing, stirring, and the like. Blending, mixing, stirring, etc. may take place for a period of time from about 50 minutes to about 1000 minutes, in embodiments from about 100 minutes to about 800 minutes. Mixing and/or blending and/or stirring may occur at speeds from about 200 revolutions per minute (rpm) to about 600 rpm, in embodiments from about 300 rpm to about 500 rpm.

The combination of the two components may be held at a suitable temperature, from about −70° C. to about 65° C., in embodiments from about −20° C. to about 55° C., in other embodiments from about 0° C. to about 45° C., for a period of time of from about 1 hour to about 120 hours, in embodiments from about 2 hours to about 72 hours.

In embodiments, the two components may be combined under an inert atmosphere, such as nitrogen.

Where the first polyol includes a polyalkylene oxide and an aliphatic dicarboxylic acid, the polyalkylene oxide may be present in an amount from about 70% by weight to about 100% by weight of the first polyol, in embodiments from about 75% by weight to about 95% by weight of the first polyol, while the amount of aliphatic dicarboxylic acid may be present in an amount from about 0% by weight to about 30% by weight of the first polyol, in embodiments from about 5% by weight to about 25% by weight of the first polyol.

In some embodiments, the aliphatic polyester macromer utilized as the first polyol may be formed by combining adipoyl chloride with a PEG such as PEG 600.

In embodiments, it may be desirable to add alumina to the aliphatic polyester macromer. The alumina may be acidic, basic, or neutral; in embodiments neutral alumina may be used. The amount of alumina added to the aliphatic polyester macromer may vary from about 10% to about 150% by weight of the aliphatic polyester macromer, in embodiments from about 50% to about 100% by weight of the aliphatic polyester macromer.

Once selected, the first polyol can be reacted with a polyisocyanate to produce an isocyanate end-capped polyol. Suitable isocyanates for endcapping the polyol include aromatic, aliphatic and alicyclic polyisocyanates, in embodiments diisocyanates. Examples include, but are not limited to, aromatic diisocyanates such as 4,4'-oxybis(phenyl isocyanate), 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate or tetramethylxylylene diisocyanate; aliphatic diisocyanates such as 2,4,6-trimethyl-1,3-phenylene diisocyanate (sold as DESMODURS®), tetramethylene diisocyanate, hexamethylene diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate or hydrogenated trimethylxylylene diisocyanate. In embodiments, combinations of the foregoing isocyanates may be utilized.

In some useful embodiments, diisocyanates such as a toluene diisocyanate (TDI), 4,4'-diphenylmethane diisocyanate (MDI), 1,6-hexamethylene diisocyanate (HMDI) and isophorone diisocyanate (IPDI) may be utilized to endcap the polyol. An aliphatic diisocyanate, such as hexamethylene diisocyanate, can be utilized in some embodiments.

The ratio of diisocyanate to the first polyol can be from about 1:1 to about 10:1, more in embodiments from about 2:1 to about 6:1. In some embodiments, the ratio of diisocyanate to polyol can be from about 2:1 to about 4:1.

In accordance with the present disclosure, the diisocyanate and first polyol may be combined and the end-capping reaction is allowed to proceed. The diisocyanate and first polyol can be combined by any means within the purview of those skilled in the art, including mixing or stirring. In one embodiment, the diisocyanate and first polyol may be combined by stirring for a period of time from about 1 hour to about 24 hours, in embodiments for a period of time from about 2 hours to about 18 hours, in other embodiments for a period of time from about 3 hours to about 8 hours.

The diisocyanate and first polyol can be heated to enhance the rate of the end-capping reaction at a temperature from about 40° C. to about 140° C., in embodiments at a temperature from about 50° C. to about 130° C., in other embodiments at a temperature from about 60° C. to about 120° C.

In some embodiments, the diisocyanate and first polyol may be mixed under an inert atmosphere, such as nitrogen.

In embodiments, the resulting diisocyanate-functional compounds of the present disclosure may be of the following formula:

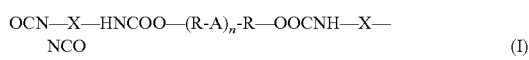
$$\text{OCN—X—HNCOO—(R-A)}_n\text{-R—OOCNH—X—NCO} \tag{I}$$

wherein X is an alicyclic, aliphatic or aromatic group; A (if present) is a group derived from an aliphatic dicarboxylic acid or derivative thereof; R can be the same or different at each occurrence and may be a group derived from a polyalkylene oxide; and n is a number from about 0 to about 10, in embodiments from about 1 to about 4.

After the end-capping reaction has occurred, a second polyol can be added and allowed to react with the free isocyanate group of the isocyanate end-capped polyol. Suitable second polyols which may react with the free isocyanate of the diisocyanate end-capped polyol include, but are not limited to, polyhydric alcohols such as ethylene glycol, diethylene glycol, triethylene glycol, polyalkylene oxides such as polyethylene glycol ("PEG"), PEG adipate, propylene glycol, dipropylene glycol, polypropylene glycol ("PPG"), tetraethylene glycol, 1,3-butanediol, 1,4-butanediol, 1,2,4-butanetriol, glycerol, trimethylol propane, 1,2,5-hexanetriol, 1,2,6-hexanetriol, polycaprolactone triol, polylactide triol, 4,4'-dihydroxyphenylpropane, 4,4'-dihydroxyphenylmethane, bis(hydroxyethyl)terephthalate, cyclohexane dimethanol, furan dimethanol, pentaerythritol, glucose, sucrose, sorbitol, and the reaction products of such polyols with propylene oxide and/or ethylene oxide. Other polyols which may be utilized include poloxamers such as polyethylene oxide (PEO) copolymers with polypropylene oxide (PPO) such as the triblock PEO-PPO copolymers commercially available as PLURONICS® from BASF Corporation (Mt. Olive, N.J.). Combinations of the foregoing polyols may be utilized in embodiments. The result of this reaction is a polyurethane.

The second polyol may have a weight average molecular weight ranging from about 50 to about 5000, in embodiments from about 100 to about 3000, and a functionality of from about 2 to about 6.

In some embodiments, a polyethylene glycol may be utilized as the second polyol. As used herein, polyethylene glycol generally refers to a polymer with a molecular weight of less than about 50,000. PEGs provide excellent water retention, flexibility and viscosity in the synthetic composition of the present disclosure. The molecular weight of the polyethylene glycol can vary depending upon the intended end use of the biocompatible composition, i.e., adhesive or sealant. In some embodiments, the molecular weight of the PEG utilized as the second polyol can be from about 100 to about 20,000, in embodiments from about 500 to about 10,000, in other embodiments from about 1,000 to about 5,000.

The ratio of second polyol to diisocyanate end-capped polyol can be from about 1:1 to about 20:1, in embodiments from about 2:1 to about 6:1, in other embodiments from about 2:1 to about 4:1.

In embodiments, the second polyol and the isocyanate end-capped polyol can be combined by stirring for a period of time of from about 1 to about 72 hours, in embodiments for a period of time of from about 2 to about 24 hours, in other embodiments for a period of time from about 3 to about 18 hours.

The second polyol and the isocyanate end-capped polyol can be heated to enhance the rate of the functionalizing reaction at a temperature of from about 40° C. to about 100° C., in embodiments at a temperature of from about 50° C. to about 80° C., in other embodiments at a temperature of from about 55° C. to about 70° C.

After the reaction of the second polyol with the free isocyanate of the diisocyanate end-capped polyol is completed, a second polyisocyanate may be added to the resulting polyurethane and allowed to react with the free hydroxyl end groups of the second polyol on the polyurethane, thereby forming an isocyanate-functional polyurethane prepolymer. Suitable isocyanates which may be utilized as the second polyisocyanate to further functionalize these polyurethanes by reacting with their free hydroxy end groups include those described above for producing the isocyanate-functional polyol. In embodiments, diisocyanates such as toluene diisocyanate (TDI), 4,4'-diphenylmethane diisocyanate (MDI), 2,4,6-trimethyl-1,3-phenylene diisocyanate, 1,6-hexamethylene diisocyanate (HMDI) and isophorone diisocyanate (IPDI) may be utilized as the second isocyanate to further functionalize these hydroxy end groups. An aliphatic diisocyanate, such as hexamethylene diisocyanate, can be utilized in some embodiments.

The ratio of second polyisocyanate to polyurethane can be from about 2:1 to about 20:1, in embodiments from about 2:1 to about 10:1, in other embodiments from about 2:1 to about 4:1.

In embodiments, the second polyisocyanate and the polyurethane may be combined by stirring for a period of time of from about 1 hour to about 24 hours, in embodiments from about 2 to about 18 hours, in other embodiments from about 3 to about 8 hours.

The second polyisocyanate and polyurethane can be heated to enhance the rate of the end-capping reaction at a temperature of from about 40° C. to about 140° C., in embodiments at a temperature from about 50° C. to about 120° C., in other embodiments at a temperature of from about 60° C. to about 100° C.

In some cases the reaction of the second polyol with free isocyanates on the isocyanate end-capped material to form a polyurethane and the reaction of the polyurethane with additional polyisocyanate occurs, at least in part, simultaneously.

The resulting isocyanate-functional polyurethane prepolymer may be linear or can have a branched or star configuration. The molecular weight of the isocyanate-functional polyurethane prepolymer can be from about 200 to about 50,000, in embodiments, from about 500 to about 20,000, in other embodiments from about 1000 to about 10,000.

The isocyanate-functional polyurethane prepolymer and foam control agent utilized to form an adhesive and/or sealant of the present disclosure may be combined utilizing any method within the purview of those skilled in the art, including mixing, blending, and the like. For example, in some embodiments the isocyanate-functional polyurethane prepolymer and the foam control agent may be combined using mixing with a simple device such as a spatula. In other embodiments, the isocyanate-functional polyurethane prepolymer and foam control agent may be combined by simply placing the two components into a first syringe and expelling the contents of the first syringe into a second syringe, followed by expelling the contents of the second syringe into the first syringe, and repeating this process between the two syringes until the components are mixed.

Thus, in some embodiments, the isocyanate-functional polyurethane prepolymer may be combined with the foam control agent prior to administration, wherein the foam control agent does not perform its function until administration of the isocyanate-functional polyurethane prepolymer and formation of an adhesive or sealant in situ.

In other embodiments, the isocyanate-functional polyurethane prepolymer may be combined with the foam control agent at the time of administration. For example, it may be useful to combine an acetylenic diol based foam control agent with the isocyanate-functional polyurethane prepolymer at the time of administration. Methods for combining the isocyanate-functional polyurethane prepolymer and the foam control agent at the time of administration are within the purview of those skilled in the art and include, for example, dispensing the isocyanate-functional polyurethane prepolymer and foam control agent from a conventional adhesive dispenser, which typically provides mixing of the first and second components prior to the dispenser. Such dispensers are disclosed, for example, in U.S. Pat. Nos. 4,978,336, 4,361,055, 4,979,942, 4,359,049, 4,874,368, 5,368,563, and 6,527,749, the entire disclosures of each of which are incorporated by reference herein.

The amount of foam control agent added to an isocyanate-functional polyurethane prepolymer may vary from about 0.05% to about 2% by weight of the biocompatible composition, i.e., the adhesive/sealant matrix to which it is added, in embodiments from about 0.1% to about 0.6% by weight of the adhesive/sealant matrix to which it is added.

The compositions of the present disclosure, i.e., the isocyanate-functional polyurethane prepolymers in combination with foam control agents, can be introduced into a patient where they cross-link in situ upon exposure to moisture in the tissue being sealed and/or adhered to form a biocompatible adhesive or sealant. The isocyanate-functional polyurethane prepolymer rapidly forms a three dimensional gel-like matrix, which reduces total surgical/operating time during a medical procedure. The foam control agent reduces or eliminates the formation of bubbles and/or foam in the resulting matrix, thereby reducing defects and weak spots in the matrix and enhancing the physical properties of the matrix.

The compositions of the present disclosure resulting from the isocyanate-functional polyurethane prepolymer in combination with a foam control agent can be used to form biocompatible compositions suitable for use in a medical/surgical capacity in place of, or in combination with, sutures, staples, clamps and the like. In one embodiment, the biocompatible compositions can be used to seal or adhere delicate tissue together, such as lung tissue, in place of conventional tools that may cause mechanical stress. The resulting biocompatible compositions can also be used to seal air and/or fluid leaks in tissue, to prevent post-surgical adhesions and to fill voids and/or defects in tissue.

The biocompatible compositions of the present disclosure can also act as drug carriers, allowing controlled release and direct delivery of a drug to a specific location in an animal, especially a human. As the compositions are synthetic, immuno-reactions in a subject's tissue may be reduced or eliminated.

Biologically active agents may be included in the compositions of the present disclosure. For example, naturally occurring polymers, including proteins such as collagen and derivatives of various naturally occurring polysaccharides such as glycosaminoglycans, can be incorporated into the compositions of the present disclosure. When these other biologically active agents also contain functional groups, the groups can react with the free isocyanate groups on the isocyanate-functional polyurethane prepolymer of the present disclosure, thereby becoming incorporated into the resulting adhesive and/or sealant.

A variety of optional ingredients including medicinal agents may also be added to the biocompatible compositions of the present disclosure. A phospholipid surfactant that provides antibacterial stabilizing properties and helps disperse other materials in the biocompatible composition may be added. Additional medicinal agents include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminic, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilators agents, antiviral agents and dysuria agents.

Imaging agents such as iodine or barium sulfate, or fluorine, can also be combined with the compositions of the present disclosure to allow visualization of the surgical area through the use of imaging equipment, including X-ray, MRI, and CAT scan equipment.

Additionally, an enzyme may be added to the biocompatible compositions of the present disclosure to increase their rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextrinase, amylase, lysozyme, oligosaccharase and the like; oligonucleotide hydrolases such as alkaline phosphatase, endoribonucleases, endodeoxyribonuclease and the like.

In some embodiments, where an enzyme is added, the enzyme may be included in a liposome or microsphere to control the rate of its release, thereby controlling the rate of degradation of the adhesive composition of the present disclosure. Methods for incorporating enzymes into liposomes and/or microspheres are within the purview of those skilled in the art.

In some embodiments, at least one linkage that is hydrolytically or enzymatically degradable may be incorporated into the isocyanate-functional polyurethane prepolymer. Linkages that are hydrolytically degradable include, but are not limited to, esters, anhydrides, and phosphoesters. Linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln(Arg)$_2$-, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Those skilled in the art will readily envision reaction schemes for incorporating enzymatically degradable linkages into the isocyanate-functional polyurethane prepolymer.

The biocompatible compositions of the present disclosure can be used for a number of different human and animal medical applications including, but not limited to, wound closure (including surgical incisions and other wounds), adhesives for adhering medical devices (including implants) to tissue, sealants and void fillers, and embolic agents. Adhesives may be used to bind tissue together either as a replacement of, or as a supplement to, sutures, staples, tapes and/or bandages. Use of the biocompatible composition as an adhesive can eliminate or substantially reduce the number of sutures normally required during current practices, and eliminate the subsequent need for removal of staples and certain types of sutures. The disclosed biocompatible composition as an adhesive can thus be particularly suitable for use with delicate tissues where sutures, clamps or other conventional tissue closure mechanisms may cause further tissue damage.

To effectuate the joining of two tissue edges, the two edges may be approximated and the biocompatible composition of the present disclosure, i.e., the isocyanate-functional polyurethane prepolymer in combination with a foam control agent, may be applied thereto. The composition then crosslinks. In this case the biocompatible composition of the present disclosure can be used as an adhesive to close a wound, including a surgical incision. The biocompatible composition of the present disclosure can thus be applied to the wound and allowed to set, thereby closing the wound.

In another embodiment, the present disclosure is directed to a method for using the biocompatible composition of the present disclosure to adhere a medical device to tissue, rather than secure two edges of tissue. In some aspects, the medical device includes an implant. Other medical devices include, but are not limited to, pacemakers, stents, shunts and the like. In some embodiments, depending on the composition of the medical device, a coating may be required on the medical device. In some cases such a coating can include the isocyanate-functional polyurethane prepolymer of the present disclosure, optionally in combination with a foam control agent. Generally, for adhering a device to the surface of animal tissue, the isocyanate-functional polyurethane prepolymer can be applied to the device, the tissue surface, or both. The device, isocyanate-functional polyurethane prepolymer and tissue surface may then be brought into contact with each other and the isocyanate-functional polyurethane prepolymer is allowed to set, thereby adhering the device and tissue surface to each other. In embodiments the foam control agent may be applied to the same surface, i.e., the device or tissue surface, as the isocyanate-functional polyurethane prepolymer; in other embodiments the foam control agent may be applied to a different surface than the isocyanate-functional polyurethane prepolymer. For example, the foam control agent could be applied to the tissue surface, the isocyanate-functional polyurethane prepolymer could be applied to the device, and the two combined as the device and tissue are brought into contact with each other. Similar means for combining the foam control agent and the isocyanate-functional polyurethane prepolymer at the time of administration may be readily apparent to those skilled in the art.

The present biocompatible composition can also be used to prevent post surgical adhesions. In such an application, the isocyanate-functional polyurethane prepolymer in combination with a foam control agent may be applied and cured as a layer on surfaces of internal tissues in order to prevent the formation of adhesions at a surgical site during the healing process.

When used as a sealant, the biocompatible composition of the present disclosure can be used in surgery to prevent or inhibit bleeding or fluid leakage both during and after a surgical procedure. It can also be applied to prevent air leaks associated with pulmonary surgery. The isocyanate-functional polyurethane prepolymer in combination with a foam control agent may be applied directly to the desired area in at least an amount necessary to seal off any defect in the tissue and seal off any fluid or air movement.

Additional applications include use of the biocompatible compositions as sealants for sealing tissues to prevent or control blood or other fluid leaks at suture or staple lines. In another embodiment, the biocompatible compositions can be used to attach skin grafts and position tissue flaps during reconstructive surgery. In still another embodiment, the biocompatible compositions can be used to close tissue flaps in periodontal surgery.

Application of the composition, whether as an adhesive or sealant, with or without other additives, can be done by any conventional means. These include dripping, brushing, or other direct manipulation of the biocompatible composition on the tissue surface, or spraying of the biocompatible composition onto the surface. As noted above, in some embodiments the biocompatible composition may also be dispensed from a conventional adhesive dispenser.

In other embodiments, especially where the composition of the present disclosure is to be utilized as a void filler or sealant to fill a defect in an animal's body, it may be advantageous to more precisely control the conditions and extent of cross-linking; thus, it may be desirable to partially cross-link the composition prior to its use to fill a void in animal tissue. In such a case the composition of the present disclosure can be applied to the void or defect and allowed to set, thereby filling the void or defect.

In open surgery, application by hand, forceps or the like is contemplated. In endoscopic surgery, the adhesive can be delivered through the cannula of a trocar, and spread at the site by any device known in the art.

The compositions prepared by the methods of the present disclosure have a number of advantageous properties. The biocompatible composition rapidly forms a compliant gel matrix, which insures stationary positioning of tissue edges or implanted medical devices in the desired location and lowers overall required surgical/application time. The biocompatible composition forms strong cohesive bonds. It exhibits excellent mechanical performance and strength, while retaining the necessary pliability to adhere living tissue. This strength and pliability allows a degree of movement of tissue without shifting the surgical tissue edge. Additionally, the biocompatible composition can be biodegradable where hydrolytically bioabsorbable groups or enzymatic linkages are included, allowing the degradation components to pass safely through the subject's body.

Adhesives and/or sealants of the present disclosure possess excessent strength and similar physical properties. For example, when applied to porcine tissue and tested for lap shear, i.e., the pull force needed to separate two pieces of tissue, compositions of the present disclosure possessing isocyanate-functional polyurethane prepolymers in combination with a foam control agent exhibit an average increase in lap shear from about 50% to about 150%, in embodiments an average increase in lap shear from about 100% to about 140%, compared with compositions possessing isocyanate-functional polyurethane prepolymers without such foam control agents. The foam control agents minimize internal defects, i.e., gas bubbles, in the resulting adhesive and/or sealant, as well as enhance the wetting properties of the adhesive and/or sealant material, i.e., lower the surface tension of the adhesive and/or sealant material.

It has also been found that the use of foam control agents as described herein does not compromise the strength degradation profile of a biocompatible composition prepared with such foam control agents, and/or the biocompatibility of the adhesive and/or sealants of the present disclosure obtained from these biocompatible compositions. This is somewhat surprising as these foam control agents may be expected to have adverse effects on these characteristics. For example, additives such as foam control agents may be reactive with the adhesive system and/or contain cytotoxic agents that can compromise the biocompatibility of an adhesive and/or sealant produced with such additives. In addition, additives such as foam control agents may migrate to the surface of the adhesive and/or sealant and thus compromise adhesion to a substrate to which the adhesive and/or sealant is applied. However, adhesives and/or sealants of the present disclosure possessing these additives did not possess these adverse characteristics; rather, the compositions of the present disclosure had minimal swelling and possessed a straight line degradation profile over time, making the compositions well suited for adhesive and sealant applications, as well as useful as drug delivery vehicles.

The resulting biocompatible compositions of the present disclosure are safe, possess enhanced adherence to tissue, have enhanced stability, are biocompatible, have hemostatic potential, have low cost, and are easy to prepare and use. By varying the selection of the polymer components, the strength and elasticity of the biocompatible composition can be controlled, as can the gelation time.

The following Examples are being submitted to illustrate embodiments of the present disclosure. These Examples are intended to be illustrative only and are not intended to limit the scope of the present disclosure. Also, parts and percentages are by weight unless otherwise indicated.

Example 1

Adipoyl chloride (commercially available from Fluka Chemical Corp., Ronkonkoma, N.Y.) was vacuum distilled at about 2.9 torr at about 88° C. PEG 600 (commercially available from Sigma Aldrich, St. Louis, Mo.) was heated to about 65° C. for about 3 hours while bubbling dry nitrogen into the PEG 600. About 275 grams of PEG 600 were dissolved in about 730 grams of tetrahydrofuran (THF). About 53 grams of pyridine were dissolved in about 199 grams of THF. The PEG 600 solution was chilled in an ice bath for about 10 minutes under stirring.

About 56 grams of adipoyl dichloride were dissolved in about 653 ml of THF. The adipoyl chloride solution and the PEG 600 solution were combined. The pyridine solution was then added dropwise at a rate of about 100 drops per minute until completely added. The solution remained under stirring for a period of about 2 hours. The solution initially remained in the ice bath. The ice bath remained in an ambient environment and the ice was allowed to reach room temperature. The material was then filtered and the filtrate was collected and concentrated using a ROTAVAPOR® rotary evaporator (BÜCHI Labortechnik AG) until the volume was reduced by about 75%. The solution was then precipitated in about 2.5 liters ethyl ether. The precipitate, PEG 600 adipate, was dried under vacuum.

About 195 grams of the extracted PEG 600 adipate produced above (sometimes referred to herein as degradable PEG) was combined with about 100 grams of about 80% toluene 2,4-diisocyanate (TDI) (from Sigma Aldrich). The PEG 600 adipate and TDI were heated to about 65° C. and mixed at about 150 revolutions per minute (RPM) for about 4 hours under static nitrogen. Upon completion of heating, the resulting product was obtained by reducing the bath temperature to about 55° C., adding petroleum ether, and mixing at about 300 rpm for about 20 minutes followed by decanting (this step was repeated three times). The resulting material, TDI functionalized PEG 600 adipate, was placed under vacuum and dried overnight at less then about 50 mTorr. The resulting product was an isocyanate-functional polyurethane prepolymer of the present disclosure.

Trimethylolpropane (TMP) (commercially available from Sigma Aldrich, St. Louis, Mo.) was heated to about 110° C. for about 2 hours while bubbling dry nitrogen into the TMP. About 100 grams of the TDI functionalized PEG 600 adipate was then combined with about 1 gram of the TMP. The materials were heated to about 65° C. and mixed at about 50 rpm under static nitrogen for about 72 hours. The resulting material was cooled to about 25° C. and transferred into syringes, which were stored in a dry box. The final material, an isocyanate-functional polyurethane prepolymer of the present disclosure, was tested for isocyanate levels as well as IR analysis. The final NCO value was about 3%.

Example 2

Foam control agents were added to the isocyanate-functional polyurethane prepolymers of Example 1 above, and compared with an untreated isocyanate-functional polyurethane prepolymer of Example 1 as a control. The foam control agent utilized was SURFYNOL® MD-20, a non-silicone solvent-free liquid defoamer from Air Products and Chemicals, Inc. (Allentown, Pa.). Three untreated isocyanate-functional polyurethane prepolymers were utilized as a control. Various amounts of SURFYNOL® MD-20 were added to about 0.2 grams of the above isocyanate-functional polyurethane prepolymers from Example 1. Both the control and isocyanate-functional polyurethane prepolymers with defoamer were subjected to a lap shear test.

Briefly, the lap shear test was as follows. The control and the isocyanate-functional polyurethane prepolymers with defoamer were applied to porcine tissue. Shear forces of the adhesives were tested using a porcine intestine substrate cut to an area of about 1.5×4.5 cm. The sample was applied over an area of about 1.5×1 cm. Another piece of substrate was placed over the applied area of adhesive. A weight of about 20 grams was put on top of both substrates for about 30 seconds to ensure proper bonding of the material and to control thickness of the adhesive. The adhesive was left to cure for about 4.5 hours. A tensiometer was used to measure the shear force exerted by the adhesive bond created between both substrates.

The results of the lap shear test for both the controls and the isocyanate-functional polyurethane prepolymers with defoamer, including the amounts of defoamer added, are set forth below in Table 1:

TABLE 1

| Sample | Amount SURFYNOL® MD-20 | Lap Shear (5 Minutes) |
| --- | --- | --- |
| 1 | 0.1% | 1.891 Kg |
| 2 | 0.5% | 2.28 Kg |
| 3 | 1% | 0.818 Kg |
| 4 | 0% (control) | 0.996 Kg |
| 5 | 0% (control) | 0.886 Kg |
| 6 | 0.5% | 1.88 Kg |
| 7 | 0% (control) | 1.1 Kg |
| 8 | 0.5% | 2.15 Kg |

With respect to the results observed with the foam control agent at 1%, without wishing to be bound by any theory, it is believed the increase in foam control agent caused the adhesive to be more hydrophobic and thus less adhesive with lower lap shear.

Example 3

A second foam control agent was combined with the isocyanate-functional polyurethane prepolymers produced above in Example 1. The defoamer utilized in this Example was DSP Emulsion from Dow Corning, a silicone-based emulsion defoamer (86% water and polydimethyl siloxane). Various amounts of DSP emulsion were added to about 0.2 grams of the above isocyanate-functional polyurethane prepolymers of Example 1 above, with an untreated isocyanate-functional polyurethane prepolymer utilized as a control. Both the control and isocyanate-functional polyurethane prepolymers with defoamer were subjected to a lap shear test as described above in Example 1. The results for both the control and the isocyanate-functional polyurethane prepolymers with defoamer, including the amounts of defoamer added, are set forth below in Table 2:

TABLE 2

| Amount of DSP Emulsion | Lap Shear (5 Minutes) |
| --- | --- |
| 0% (control) | 1.086 Kg |
| 3% | 0.724 Kg |
| 0.5% | 1.984 Kg |
| 0.1% | 1.928 Kg |

As can be seen from Table 2 above, the lap shear for samples having 0.5% or 0.1% of the DSP emulsion as a defoamer nearly doubled.

The above samples with defoamer were also subjected to cytotoxicity testing, volume swelling, and in vitro strength profile tests to determine their degradation profile.

Cytotoxicity testing was performed using methods of standard ISO 10993 part 5.

For the volume swelling tests, adhesive films were cast on a dry, flat glass surface using a stainless steel doctor blade, where the thickness was precisely controlled using a built-in micrometer. The films were left to cure at room temperature for about 24 hours under a hood. The purpose of the slow cure conditions was to minimize bubble formation (foaming), which could lead to rough heterogeneous surfaces, causing inaccuracies in volume measurements.

A metal punch was used to cut circular films with a fixed diameter (about 7.3 mm). The thickness and weight of each film were measured before they were placed in a separate labeled container with a 10 ml buffer solution of a known pH of about 7.2. The closed vials were then immersed in a 37° C. water bath. The results were based on the average of 5 films per sample per measurement (n=5).

The films were taken out of the bath at different time points and dried by tapping them slightly with a paper towel. Weight and size measurements were then taken.

For the in vitro strength profile tests, 2 rigid polyurethane test blocks were used per sample. Test blocks were soaked in water prior to adhesive application. About 0.05 ml adhesive was applied to one test block using a syringe pump. A second test block was then mated to the first and a 20 gram weight was balanced on top of the resulting construct for about 5 minutes. After about 1 hour, samples were then placed into a glass jar filled with water for about 24 hours before tensile testing. Samples were tested at time 0 by mounting the test blocks onto a Sintech 1/G MTS using screw action grips and loaded to failure at 2 inch/minutes. The remaining samples were submerged in Sorenson buffer and placed into a 37° C. bath until the next time point test.

The compositions were found to be biocompatible, with less swelling (P=0.003) compared with the control sample lacking defoamer, and had a straight line degradation profile, i.e., the addition of the defoamer did not adversely affect the degradation of the composition.

Example 4

An additional sample of an isocyanate-functional prepolymer was prepared as described above in Example 1 and tested with an additional defoamer. N-methylpyrrolidone (NMP) was used as a solvent in preparing the compositions.

The other defoamer utilized was 0.5% of MED-340, a polydimethyl siloxane antifoaming agent from NuSil Technology (Carpinteria, Calif.). Isocyanate-functional polyurethane prepolymers from Example 1 without any defoamers were utilized as a control. The samples were subjected to lap shear tests as described above in Example 1. The results of the lap shear test are set forth below in Table 3.

TABLE 3

| Sample | Lap Shear (g @ 5 minutes) |
| --- | --- |
| w/0.5% MED-340 | 1866 |
| Control (without antifoaming agent) | 1322 |

Example 5

An isocyanate-functional prepolymer was prepared as described above in Example 1 where 25% of the ether component was substituted with butane diol. The butane diol was added to the polymer in order to slow the degradation process of the final material. The components utilized to form this material are set forth below in Table 4.

TABLE 4

| Material | Amount |
| --- | --- |
| 155.5 grams of PEG 600 = 0.260 moles | 75% |
| 7.89 grams of Butane diol = 0.088 moles | 25% (total 0.348 moles of Diols) |
| 36.832 grams of Pyridine = 0.466 moles | 1.49 molar ratio |
| 42.836 grams of Adipoyl chloride = 0.234 moles | 2.0 molar ratio |

The ratio of PEG to adipoyl chloride was about 3:2.

The material was produced as follows. About 155.5 grams of PEG and about 7.89 grams of butane diol were dried together at a molar ratio of about 3:1 in a clean, dry, 1 liter flask. About 218.6 grams of THF was added to the flask to dissolve the PEG and butane diol, followed by the addition of about 36.832 grams of pyridine. At the same time, a 2 liter, two neck, flask was charged with about 444.28 grams of THF followed by the addition of about 42.836 grams of adipoyl chloride. The 2 liter flask and its contents were chilled by placing the flask in an ice bath for about 10 minutes. A mechanical stirrer was placed in the 2 liter flask and the PEG/butane diol mixture was added drop wise at a rate of about 120 drops per minute, while the mechanical stirrer was set at about 165 revolutions per minute for about 3 hours. After this time, the stirring speed was increased to about 250 revolutions per minute with mixing continuing overnight and the flask remaining in the ice bath.

The material was then filtered using a fine filter funnel. A small amount of THF was purged through the funnel before the product was filtered. The THF was removed using a ROTAVAPOR® rotary evaporator. The resulting material was precipitated with approximately 1 liter of ethyl ether, followed by decanting and washing two times with 1 liter of ethyl ether (for each washing). The resulting material, a PEG/butane diol adipate, was then placed in a vacuum oven for about three days to remove any remaining ethyl ether.

The material thus obtained was then functionalized with TDI as described above in Example 1. About 69 grams of the extracted PEG/butane diol adipate produced above was combined with about 36.31 grams of toluene 2,4-diisocyanate (TDI) (from Sigma Aldrich) following the conditions set forth in Example 1 to obtain an isocyanate-functional polyurethane prepolymer of the present disclosure.

The prepolymer was subjected to gamma radiation at a dosage of about 27-45 kGy. Samples of the prepolymer with NMP solvent and NMP in combination with Dow Corning Medical Antifoam A compound (sometimes referred to herein as DCMA from Dow Corning) were also subjected to gamma radiation. Table 5 below summarizes lap shear results and viscosity for these samples both before and after radiation.

TABLE 5

Lap Shear and Viscosity

| | Before Radiation | | After Radiation | |
|---|---|---|---|---|
| | Lap Shear | @ 5.2 rpm Viscosity (cP) | Lap Shear | @ 5.2 rpm Viscosity (cP) |
| Control | 920 g | 45000 | 1516 g | 89000 |
| w/10% NMP | 878 g | 16000 | 1696 g | 29000 |
| w/10% NMP and 0.5% DCMA | 1340+ g (failed at the grips) | 26000 | 1580 g | 51000 |

These same samples were also subjected to cytotoxicity testing as described above in Example 3. The amount of media (saline) used for all samples was 20 mL, which corresponded to an extraction ratio of 0.5 g/10 mL. Sterile samples used an extraction ratio of about 1 g/10 mL. After the incubation period, additional intake of media by the sample was compensated. The results of this testing demonstrated that none of the samples exhibited any cytotoxicity.

The resulting isocyanate-functional polyurethane prepolymer of the present disclosure, in this case an isocyanate functional PEG/butane diol adipate, was then combined with polycaprolactone triol to form a branched polymer. About 26.1 grams of the isocyanate functional PEG/butane diol adipate was combined with about 0.6 grams of polycaprolactone triol. The two were mixed at a rate of about 50 rpm under nitrogen at a temperature of about 65° C. for about 72 hours. The resulting polymer could be utilized, in embodiments, as an adhesive or sealant.

Example 6

Isocyanate-functional polyurethane prepolymers in combination with a defoamer from Example 2 (SURFYNOL® MD-20) and the isocyanate-functional polyurethane prepolymers in combination with the defoamer from Example 3 (DSP emulsion) were subjected to swelling testing as described above in Example 3. Isocyanate-functional polyurethane prepolymers in combination with $NaHCO_3$ were utilized as a control. Samples were taken at time 0, 4 hours, 26 hours, and 96 hours, at which time thickness, diameter, and weight of each sample was recorded. The volume of the sample at each time period was calculated.

Figure 7:
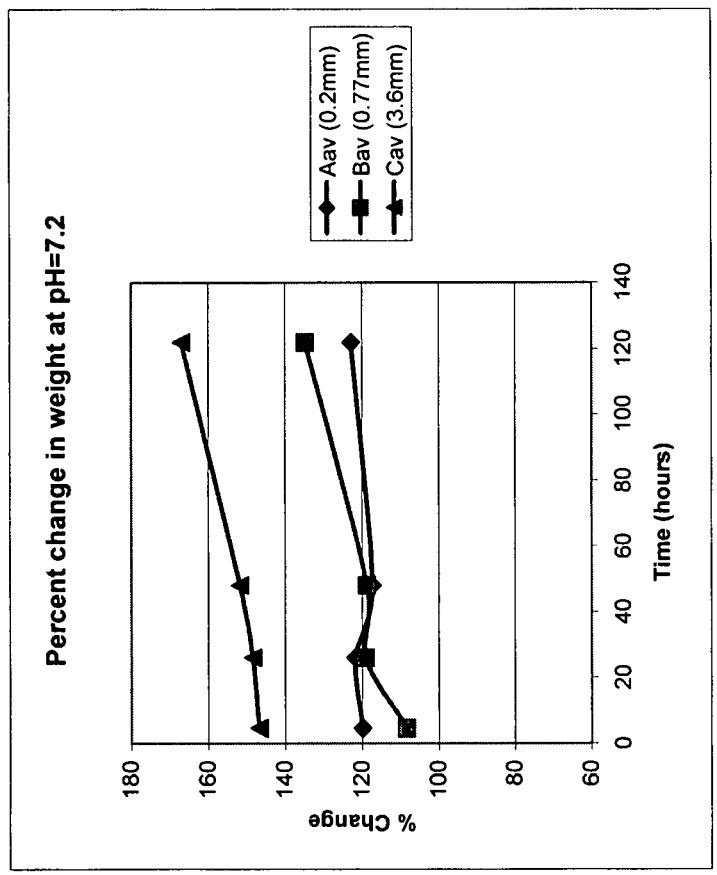
FIG. 7 is a graph depicting the average percent change in weight of the samples from FIG. 4 over time.

Results are set forth in FIGS. 1 to 10. All the data in FIGS. 1-10 labeled with "A" were for the same material. The material was 3 PEG molecules combined with 2 adipoyl chloride; the resulting polylol (PEG-Ad-PEG-Ad-PEG) was then functionalized with TDI and branched with TMP as described above in Example 1. The various foam control agents added as per the Examples above are specified on the Figures. The sample labeled with "H" in FIGS. 1, 2, 3, 9, and 10 contains butane diol in the backbone, which was produced by substituting 25% of the ether component in the polylol (i.e., PEG) with butane diol as described above in Example 5. In FIGS. 9 and 10: A was 3 PEG:2Ad; D was 4PEG:1HMDI:1Ad; E was 3PEG and Butane diol:2Ad; F was 3PEG: 1 HMDI:1Ad; G was 3 PEG, 2Ad (different viscosity from A); and H was 3PEG and Butane diol:2Ad (different viscosity from E). "A" samples in FIGS. 1, 2 and 3 with additives can be compared to "A" samples in FIGS. 4, 5 and 6, especially to $A_{average}$ (same thickness). "H" samples in FIGS. 1, 2 and 3 with additive can be compared to "H" samples in FIGS. 9 and 10.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A method comprising:
   reacting a first polyol selected from the group consisting of polyether polyols, polycaprolactone polyols, and polyhydric alcohols with a first polyisocyanate selected from the group consisting of aromatic, aliphatic and alicyclic diisocyanates, to produce an isocyanate end-capped polyol;
   reacting the isocyanate end-capped polyol with a second polyol to produce a polyurethane;
   reacting the polyurethane with a second polyisocyanate to produce at least one isocyanate-functional polyurethane prepolymer;
   contacting the at least one isocyanate-functional polyurethane prepolymer with at least one foam control agent;

applying the at least one isocyanate-functional polyurethane prepolymer with at least one foam control agent to tissue; and allowing the at least one isocyanate-functional polyurethane prepolymer to react with the tissue, wherein the at least one isocyanate-functional polyurethane prepolymer crosslinks upon contact with water in the tissue thereby forming a biocompatible composition possessing a strength profile that is not compromised by the presence of the foam control agent.

2. The method of claim 1, wherein the step of reacting the first polyol with the first polyisocyanate comprises reacting a first polyol selected from the group consisting of polyether polyols, polycaprolactone polyols, polyhydric alcohols, polyalkylene oxides, poloxamers, and combinations thereof.

3. The method of claim 1, wherein the step of reacting the first polyol with the first polyisocyanate comprises reacting a first polyol comprising the reaction product of a polyalkylene oxide in combination with an aliphatic dicarboxylic acid.

4. The method of claim 1, wherein the step of reacting the first polyol with the first polyisocyanate comprises utilizing a diisocyanate selected from the group consisting of 4,4'-oxybis(phenyl isocyanate), 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, tetramethylxylylene diisocyanate, 2,4,6-trimethyl-1,3 phenylene diisocyanate, tetramethylene diisocyanate, hexamethylene diisocyanate, lysine diisocyanate, 2-methylpentane-1,5-diisocyanate, 3-methylpentane-1,5-diisocyanate, 2,2,4-trimethylhexamethylene diisocyanate, isophorone diisocyanate, cyclohexane diisocyanate, hydrogenated xylylene diisocyanate, hydrogenated diphenylmethane diisocyanate, hydrogenated trimethylxylylene diisocyanate, and combinations thereof.

5. The method of claim 1, wherein the step of reacting the first polyol with the first polyisocyanate comprises utilizing a diisocyanate selected from the group consisting of toluene diisocyanate, 4,4'-diphenylmethane diisocyanate, 1,6-hexamethylene diisocyanate, isophorone diisocyanate, and hexamethylene diisocyanate.

6. The method of claim 1, wherein the step of reacting the isocyanate end-capped polyol with a second polyol comprises utilizing a second polyol selected from the group consisting of ethylene glycol, diethylene glycol, triethylene glycol, polyethylene glycol, polyethylene glycol adipate, propylene glycol, dipropylene glycol, polypropylene glycol, tetraethylene glycol, 1,3-butanediol, 1,4-butanediol, 1,2,4-butanetriol, glycerol, trimethylol propane, 1,2,5-hexanetriol, 1,2,6-hexanetriol, polycaprolactone triol, polylactide triol, 4,4'-dihydroxyphenylpropane, 4,4'-dihydroxyphenylmethane, bis(hydroxyethyl)terephthalate, cyclohexane dimethanol, furan dimethanol, pentaerythritol, glucose, sucrose, sorbitol, polyethylene oxide copolymers with polypropylene oxide, and combinations thereof.

7. The method of claim 1, wherein the step of reacting the polyurethane with the second polyisocyanate comprises utilizing a diisocyanate selected from the group consisting of 4,4'-oxybis(phenyl isocyanate), 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, tetramethylxylylene diisocyanate, 2,4,6-trimethyl-1,3 phenylene diisocyanate, tetramethylene diisocyanate, hexamethylene diisocyanate, lysine diisocyanate, 2-methylpentane-1,5-diisocyanate, 3-methylpentane-1,5-diisocyanate, 2,2,4-trimethylhexamethylene diisocyanate, isophorone diisocyanate, cyclohexane diisocyanate, hydrogenated xylylene diisocyanate, hydrogenated diphenylmethane diisocyanate, hydrogenated trimethylxylylene diisocyanate, and combinations thereof.

8. The method of claim 1, wherein the at least one foam control agent comprises a hydrophobic component, optionally in combination with a carrier vehicle, optionally in combination with an emulsifier.

9. The method of claim 8, wherein the hydrophobic component is selected from the group consisting of treated silica, waxes, silicones, silicone derivatives, diols, and combinations thereof.

10. The method of claim 8, wherein the carrier vehicle is selected from the group consisting of mineral oils, vegetable oils, silicone oils, alcohols, glycols, water, and combinations thereof, and the emulsifier is selected from the group consisting of ethoxylated alkylphenols, sorbitan esters, polyethylene glycol esters, and combinations thereof.

11. The method of claim 8, wherein the carrier vehicle is selected from the group consisting of liquid paraffin, mixtures of saturated hydrocarbons, cyclic hydrocarbons, almond oil, apricot kernel oil, avocado oil, castor oil, hydrogenated castor oil, coconut oil, hydrogenated coconut fatty glycerides, corn oil, evening primrose oil, jojoba oil, linseed oil, olive oil, palm oil, peanut oil, rapeseed oil, safflower oil, sesame oil, soybean oil, sunflower oil, wheat germ oil, cotton seed oil, palm kernel oil, polydimethyl siloxanes, cyclic dimethyl polysiloxanes, dimethiconol, ethanol, mannitol, sorbitol, glycerol, xylitol, propylene glycol, polypropylene glycol, ethylene glycol, polyethylene glycol, and combinations thereof, and the emulsifier is selected from the group consisting of nonylphenol ethoxylate, sorbitan tristearate, sorbitan sesquioleate, sorbitan monooleate, sorbitan laurate, sorbitan oleate, polyethylene glycol stearyl ether, polyethylene glycol stearate, polyethylene glycol distearate, polyethylene glycol palmitostearate, polyethylene glycol dilaurate, polyethylene glycol dioleate, and combinations thereof.

12. The method of claim 1, wherein the foam control agent is present in an amount from about 0.05% to about 2% by weight of the biocompatible composition.

13. A biocompatible adhesive comprising the biocompatible composition produced by the process of claim 1.

14. A biocompatible sealant comprising the biocompatible composition produced by the process of claim 1.

15. A method for closing a wound comprising:
applying the biocompatible composition produced by the method of claim 1 to said wound; and
allowing the biocompatible composition to set thereby closing said wound.

16. A method for filling a void in animal tissue comprising:
applying the biocompatible composition produced by the method of claim 1 to said void; and
allowing the biocompatible composition to set thereby filling said void.

17. A method for adhering a medical device to a surface of animal tissue comprising the steps of:
applying the biocompatible composition produced by the method of claim 1 to said device, said surface or both;
bringing the device, biocompatible composition and surface into contact with each other; and
allowing the biocompatible composition to set thereby adhering the device and surface to each other.

* * * * *